(12) United States Patent
Maliga et al.

(10) Patent No.: US 7,534,936 B2
(45) Date of Patent: May 19, 2009

(54) TRANSGENIC PLANTS HAVING TRANSFORMED PLASTID GENOMES AND PROGENY THEREOF

(75) Inventors: Pal Maliga, East Brunswick, NJ (US); Sylvie Corneille, Lyons (FR); Kerry Lutz, Lawrenceville, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 487 days.

(21) Appl. No.: 10/473,207

(22) PCT Filed: Mar. 29, 2002

(86) PCT No.: PCT/US02/09537

§ 371 (c)(1),
(2), (4) Date: Mar. 10, 2004

(87) PCT Pub. No.: WO02/079409

PCT Pub. Date: Oct. 10, 2002

(65) Prior Publication Data

US 2004/0163145 A1    Aug. 19, 2004

Related U.S. Application Data

(60) Provisional application No. 60/279,615, filed on Mar. 29, 2001.

(51) Int. Cl.
*A01H 5/00* (2006.01)
*C12N 15/82* (2006.01)
(52) U.S. Cl. .................................. 800/298; 800/278
(58) Field of Classification Search ........................ None
See application file for complete search history.

(56) References Cited

U.S. PATENT DOCUMENTS

| | | | |
|---|---|---|---|
| 5,614,395 A | 3/1997 | Ryals et al. | |
| 5,686,079 A | 11/1997 | Curtiss, III et al. | |
| 5,877,402 A | 3/1999 | Maliga et al. | |
| 6,110,736 A | 8/2000 | Hodges et al. | |
| 6,149,919 A | 11/2000 | Domenighini et al. | |
| 6,297,054 B1 | 10/2001 | Maliga et al. | |
| 6,376,744 B1 | 4/2002 | Maliga et al. | |
| 6,388,168 B1 | 5/2002 | Maliga et al. | |
| 6,472,586 B1 | 10/2002 | Maliga et al. | |
| 6,849,778 B1 * | 2/2005 | Staub et al. ................. | 800/278 |

FOREIGN PATENT DOCUMENTS

| | | |
|---|---|---|
| EP | 0 430 645 A2 | 6/1991 |
| WO | WO 01/21768 A1 | 3/2001 |
| WO | WO 01/42509 A1 | 6/2001 |
| WO | WO 01/77353 A2 | 10/2001 |

OTHER PUBLICATIONS

Khan, M.S. "Fluorescent antibiotic resistance marker for tracking plastid transformation in higher plants"; Nature Biotechnology, 17: 910-915 (1999).
Dale, E.C. "Gene transfer with subsequent removal of the selection gene from the host genome"; Proc. Natl. Acad. Sci. USA, 88: 10558-10562 (1991).
Srivastava, V. "Single-copy transgenic wheat generated through the resolution of complex integration patterns"; Proc. Natl. Acad. Sci. USA, 96: 11117-11121 (1999).
Le, Y. "Nuclear targeting determinants of the phage P1 Cre DNA recombinase"; Nucleic Acids Research, 27(24): 4703-4709 (1999).
Lyznik, L.A. "Activity of yeast FLP recombinase in maize and rice protoplasts"; Nucleic Acids Research, 21(4): 969-975 (1993).
Lyznik, L.A. "FLP-mediated recombination of FRT sites in the maize genome"; Nucleic Acids Research, 24(19): 3784-3789 (1996).
Zoubenko, O.V. "Efficient targeting of foreign genes into the tobacco plastid genome"; Nucleic Acids Research, 22(19): 3819-3824 (1994).
Love, J. "Stringent control of transgene expression in *Arabidopsis thaliana* using the Top10 promoter system"; The Plant Journal, 21(6): 579-588 (2000).
Serino, G. "A negative selection scheme based on the expression of cytosine deaminase in plastids"; The Plant Journal, 12(3): 697-701 (1997).
Lyznik, L.A. "Heat-inducible expression of FLP gene in maize cells"; The Plant Journal, 8(2): 177-186 (1995).
Soll, J. "Protein translocation into and across the chloroplastic envelope membranes"; Plant Molecular Biology, 38: 191-207 (1998).
Adams, D. "Cre-lox Recombination in *Escherichia coli* Cells Mechanistic Differences from the in Vitro Reaction"; J. Mol. Biol., 226: 661-673 (1992).
Craig, N.L. "The Mechanism of Conservative Site-Specific Recombination"; Annu. Rev. Genet., 22: 77-105 (1988).
Lichtenstein, C. "Prospects for reverse genetics in plants using recombination"; Plant Molecular Biology, 21: v-xii (1993).
Lubben, T.H. "Chloroplast import characteristics of chimeric proteins"; Plant Molecular Biology; 12: 13-18 (1989).
Russell, S.H. "Directed excision of a transgene from the plant genome"; Mol Gen Genet, 234: 49-59 (1992).
Timko, M.P. "Structure and Expression of Nuclear Genes Encoding Polypeptides of the Photosynthetic Apparatus"; Mol Biol of the Photosynthetic Apparatus, 381-396 (1985).
Timmermans, M.C.P. "The pFF plasmids: cassettes utilising CaMV sequences for expression of foreign genes in plants"; Journal of Biotechnology, 14: 333-344 (1990).
Wasmann, C.C. "The importance of the transit peptide and the transported protein for protein import into chloroplasts"; Mol Gen Genet, 205: 446-453 (1986).

(Continued)

*Primary Examiner*—Anne R Kubelik
(74) *Attorney, Agent, or Firm*—Dann, Dorfman, Herrell and Skillman; Kathleen D. Rigaut

(57) ABSTRACT

Plants having transformed plastid genomes comprising a construct comprising attL and attR sites and a gene of interest, where the plants comprise an integrase and, optionally a selectable marker gene, and methods of making the plants.

4 Claims, 19 Drawing Sheets

OTHER PUBLICATIONS

Pizza, M. "A Genetically Detoxified Derivative of Heat-labile *Escherichia coli* Enterotoxin Induces Neutralizing . . . "; J. Exp. Med., 180: 2147-2153 (1994).

Ma, S.W. "Transgenic plants expressing autoantigens fed to mice to induce oral immune tolerance"; Nature Medicine; 3(7): 793-796 (1997).

Kuroda, H. "Complementarity of the 16S rRNA penultimate stem with sequences downstream of the AUG destabilizes the plastid mRNAs"; Nucleic Acids Research, 29-4: 970-975 (2001).

Kuroda, H. "Sequences Downstream of the Translation Initiation Codon Are Important Determinants of Translation Efficiency in Chloroplasts"; Plant Phys, 125: 430-436 (2001).

Ye, G. "Plastid-expressed 5-enolpyruvylshikimate-3-phosphate synthase genes provide high level glyphosate tolerance in tobacco"; The Plant Journal, 25(3): 261-270 (2001).

Staub, J.M. "High-yield production of human therapeutic protein in tobacco chloroplasts"; Nature Biotechnology, 18: 333-338 (2000).

Heifetz, P.B. "Genetic engineering of the chloroplast"; Biochimie, 82: 655-666 (2000).

Giddings, G. "Transgenic plants as factories for biopharmaceuticals"; Nature Biotechnology, 18: 1151-1155 (2000).

Douce, G. "Genetically Detoxified Mutants of Heat-Labile Toxin from *Escherichia coli* Are Able To Act as Oral Adjuvants"; Infection and Immunity, 67(9): 4400-4406 (1999).

Douce, G. "Mucosal immunogenicity of genetically detoxified derivatives of heat labile toxin from *Escherichia coli*"; Vaccine, 16(11/12): 1065-1073 (1998)

Barchfeld, G.L. "The adjuvants MF59 and LT-K63 enhance the mucosal and systemic immunogenicity of subunit influenza vaccine administered..in mice"; Vaccine, 17: 695-704 (1999).

Corneille, S. Efficient elimination of selectable marker genes from the plastid genome by the CRE-lox site-specific recombination . . . The Plant Journal, 27(2): 171-178 (2001).

Hajdukiewicz, P. "Multiple pathways for Cre/lox-mediated recombination in plastids" The Plant Journal, 27(2): 161-170 (2001).

Daniell, H. "Marker free transgenic plants: engineering the chloroplast gene without the use of antibiotic selection" Curr. Genet., 39: 109-116 (2001).

Tacket, C. "Immunogenicity in humans of a recombinant bacterial antigen delivered in a transgenic potato" Nature Medicine, 4(5): 607-609 (1998).

Tacket, C. "A review of oral vaccination with transgenic vegetables" Microbes and Infection, 777-783 (1999).

Tregoning, J. "Expression of tetanus toxin Fragment C in tobacco chloroplasts" Nucleic Acids Research, 31(4): 1174-1179 (2003).

Bock, R. "Transgenic Plastids in Basic Research and Plant Biotechnology" J. Mol. Biol., 312: 425-438 (2001).

Magagnoli, C. "Mutations in the A Subunit Affect Yield, Stability, and Protease Sensitivity of Nontoxic Derivatives . . . " Infection and Immunity, 64(12): 5434-5438 (1996).

Carrer, H. "Kanamycin resistance as a selectable marker to plastid transformation in tobacco"; Mol Gen Genet, 241: 49-56 (1993).

Ebinuma "Systems for the removal of a selection marker and their combination with a positive marker"; Plant Cell Rep., 20: 383-392 (2001).

* cited by examiner pKO107

P: promoter
T: terminator
*int*: integrase gene
▶ : *lox* site

*ori*: replication origin for *E. coli*
■▶ : *att* site
*neo*: kanamycin resistance gene

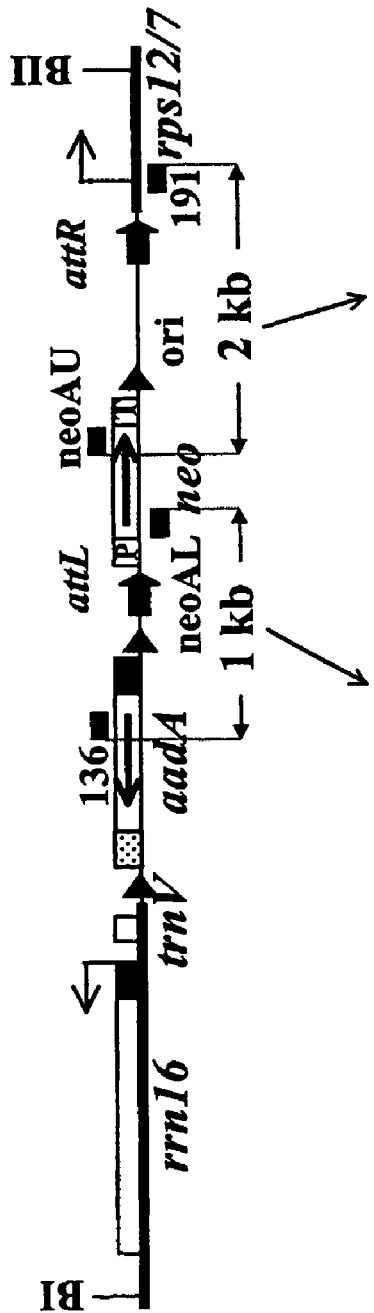
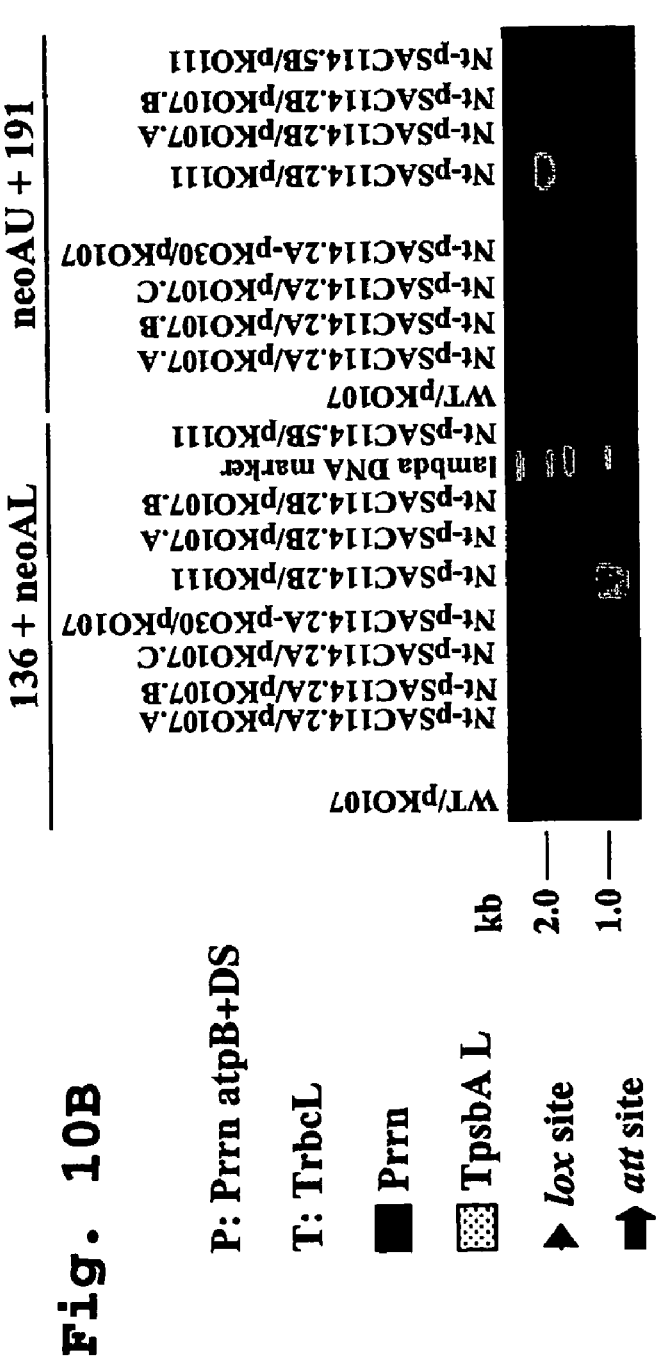
Fig. 10A
Fig. 10B

*goi*: gene of interest     P: promoter     *mg*: marker gene
*ori*: replication origin for *E. coli*     T: terminator
*int*: integrase gene     CRE: CRE recombinase
▶ : *lox* site     ➡ : *att* site

+ CRE

+ CRE

---

*goi*: gene of interest    *mg*: marker gene    P: promoter
RBS: ribosome binding site    *ori*: replication origin for *E. coli*    T: terminator
*int*: integrase gene    CRE: CRE recombinase    *aadA*: *aadA* gene
▶ : *lox* site    ➡ : *att* site Fig. 14A
```
→ |P1|Ed| int |RBS| aadA |T1|→
                                    attB
```
Fig. 14B
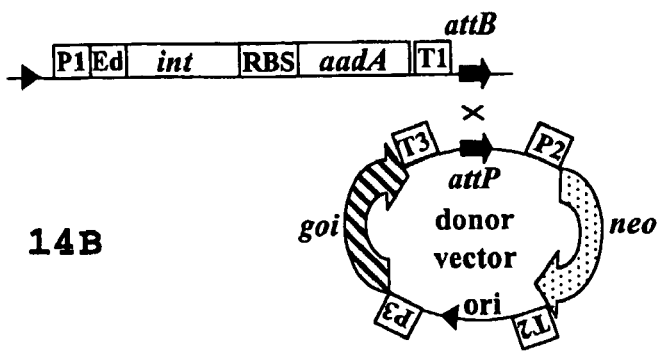
Fig. 14C
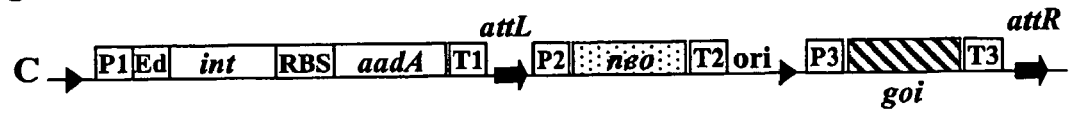
Fig. 14D
  + CRE
---
*goi*: gene of interest  *ori*: replication origin for *E. coli*  P: promoter
RBS: ribosome binding site  CRE: CRE recombinase  T: terminator
*int*: integrase gene  ➡ : *att* site
▶ : *lox* site  *neo*: kanamycin resistance gene goi: gene of interest    ori: replication origin for E. coli    P: promoter
INT: integrase           CRE: CRE recombinase                   T: terminator
▶ : lox site             ➡ : att site                           mg: marker gene P: promoter         mg: marker gene              bar: bar gene
T: terminator       ori: replication origin for E. coli
INT: integrase      CRE: CRE recombinase
▲ : lox site        ⬆ : att site

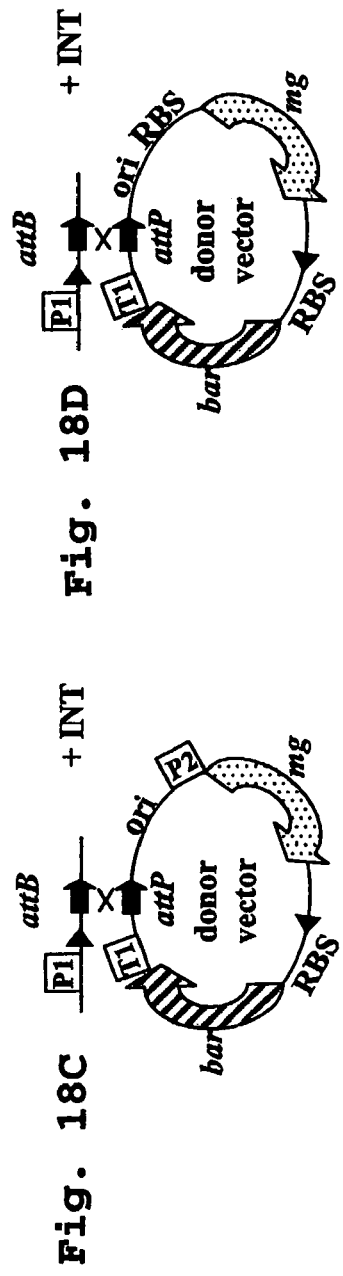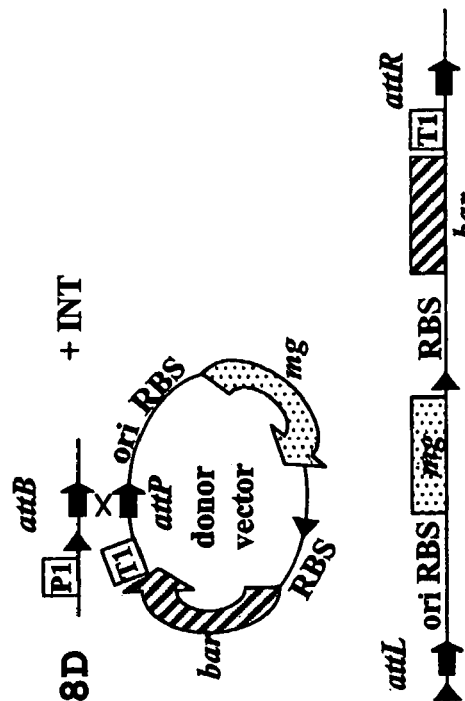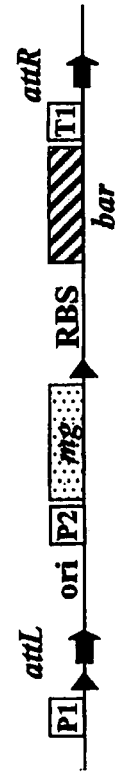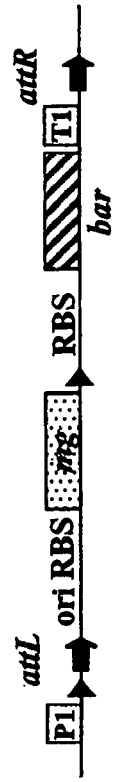

Fig. 19A
Fig. 19B
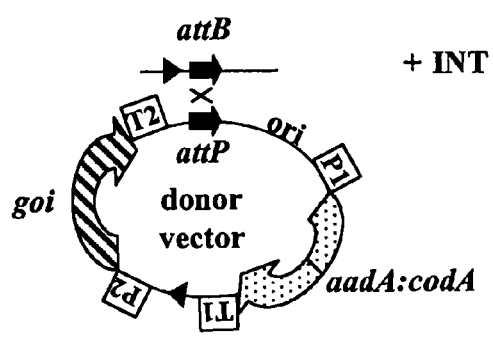
Fig. 19C
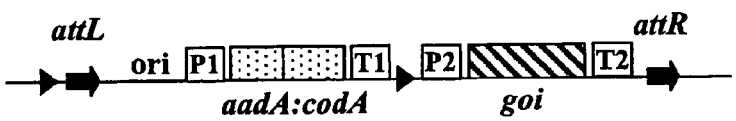
Fig. 19D
*goi*: gene of interest
*mg*: marker gene
INT: integrase
▶ : *lox* site
*ori*: replication origin for *E. coli*
CRE: CRE recombinase
➡ : *att* site
*aadA:codA*: (*aadA:codA*) marker gene
P: promoter
T: terminator

SEQUENCE LISTING

<160> NUMBER OF SEQ ID NOS: 29

<210> SEQ ID NO 1
<211> LENGTH: 46
<212> TYPE: DNA
<213> ORGANISM: Artificial Sequence
<220> FEATURE:
<223> OTHER INFORMATION: Lox site

<400> SEQUENCE: 1
agatctataa cttcgtataa tgtatgctat acgaagttat aagctt       46

<210> SEQ ID NO 2
<211> LENGTH: 46
<212> TYPE: DNA
<213> ORGANISM: Artificial Sequence
<220> FEATURE:
<223> OTHER INFORMATION: Lox site

<400> SEQUENCE: 2
ggtaccataa cttcgtataa tgtatgctat acgaagttat agatct       46

```
<210> SEQ ID NO 3
<211> LENGTH: 63
<212> TYPE: DNA
<213> ORGANISM: Artificial Sequence
<220> FEATURE:
<223> OTHER INFORMATION: attB sequence

<400> SEQUENCE: 3
ctgcagccgc ggtgcgggtg ccagggcgtg cccttgggct ccccgggcgc gtactccact      60
agt                                                                  63

<210> SEQ ID NO 4
<211> LENGTH: 1544
<212> TYPE: DNA
<213> ORGANISM: Artificial Sequence
<220> FEATURE:
<223> OTHER INFORMATION: vector insert

<400> SEQUENCE: 4
ggtaccataa cttcgtataa tgtatgctat acgaagttat agatcagctt gcatgcctgc      60
aggtcgaata tagctcttct ttcttatttc aatgatatta ttatttcaaa gataagagat     120
attcaaagat aagagataag aagaagtcaa aatttgattt ttttttttgga aaaaaaaat     180 caaaagata tagtaacatt agcaagaaga gaaacaagtt ctatttcaca atttaaacaa     240
atacaaaatc aaaatagaat actcaatcat gaataaatgc aagaaaataa cctctccttc     300
tttttctata atgtaaacaa aaaagtctat gtaagtaaaa tactagtaaa taataaaaa     360 gaaaaaaga aaggagcaat agcaccctct tgatagaaca agaaaatgat tattgctcct     420
ttcttttcaa aacctcctat agactaggcc aggatcgctc tagacattat ttgccgacta     480
ccttggtgat ctcgcctttc acgtagtgga caaattcttc caactgatct gcgcgcgagg     540
ccaagcgatc ttcttcttgt ccaagataag cctgtctagc ttcaagtatg acgggctgat     600
actgggccgg caggcgctcc attgcccagt cggcagcgac atccttcggc gcgattttgc     660
cggttactgc gctgtaccaa atgcgggaca acgtaagcac tacatttcgc tcatcgccag     720
cccagtcggg cggcgagttc catagcgtta aggtttcatt tagcgcctca aatagatcct     780
gttcaggaac cggatcaaag agttcctccg ccgctggacc taccaaggca acgctatgtt     840
ctcttgcttt tgtcagcaag atagccagat caatgtcgat cgtggctggc tcgaagatac     900
ctgcaagaat gtcattgcgc tgccattctc caaattgcag ttcgcgctta gctgataac     960 gccacggaat gatgtcgtcg tgcacaacaa tggtgacttc tacagcgcgg agaatctcgc    1020
tctctccagg ggaagccgaa gtttccaaaa ggtcgttgat caaagctcgc cgcgttgttt    1080
catcaagcct tacggtcacc gtaaccagca aatcaatatc actgtgtggc ttcaggccgc    1140
catccactgc ggagccgtac aaatgtacgg ccagcaacgt cggttcgaga tggcgctcga    1200
tgacgccaac tacctctgat agttgagtcg atacttcggc gatcaccgct tccccccatgg    1260 atccctccct acaactgtat ccaagcgctt cgaattcgcc cggagttcgc tcccagaaat    1320
atagccatcc ctgcccccctc acgtcaatcc cacgagcctc ttatccattc tcattgaacg    1380
acggcggggg agcggatcta aacttcgta taatgtatgc tatacgaagt tataagcttg    1440
atatcgaatt cctgcagccg cggtgcgggt gccagggcgt gcccttgggc tccccgggcg    1500
cgtactccac tagttctaga gcggccgcca ccgcggtgga gctc                   1544
```

<210> SEQ ID NO 5
<211> LENGTH: 1836
<212> TYPE: DNA
<213> ORGANISM: phage phiC31

<400> SEQUENCE: 5

```
ggatccatgg ctagcgacac gtacgcgggt gcttacgacc gtcagtcgcg cgagcgcgaa      60
aattcgagcg cagcaagccc agcgacacag cgtagcgcca acgaagacaa ggcggccgac     120
cttcagcgcg aagtcgagcg cgacggggc  cggttcaggt tcgtcgggca tttcagcgaa     180
gcgccgggca cgtcggcgtt cgggacgcg  gagcgcccgg agttcgaacg catcctgaac     240
gaatgccgcg ccgggcggct caacatgatc attgtctatg acgtgtcgcg cttctcgcgc     300
ctgaaggtca tggacgcgat tccgattgtc tcggaattgc tcgccctggg cgtgacgatt     360
gtttccactc aggaaggcgt cttccggcag ggaaacgtca tggacctgat tcacctgatt     420
atgcggctcg acgcgtcgca caagaatct  tcgctgaagt cggcgaagat tctcgacacg     480
aagaacccttc agcgcgaatt gggcgggtac gtcggcggga aggcgcctta cggcttcgag     540
cttgtttcgg agacgaagga gatcacgcgc aacggccgaa tggtcaatgt cgtcatcaac     600
aagcttgcgc actcgaccac tccccttacc ggacccttcg agttcgagcc cgacgtaatc     660
cggtggtggt ggcgtgagat caagacgcac aaacaccttc ccttcaagcc gggcagtcaa     720
gccgccattc acccgggcag catcacgggg ctttgtaagc gcatggacgc tgacgccgtg     780
ccgacccggg gcgagacgat tgggaagaag accgcttcaa gcgcctggga cccggcaacc     840
gttatgcgaa tccttcggga cccgcgtatt gcgggcttcg ccgctgaggt gatctacaag     900
aagaagccgg acggcacgcc gaccacgaag attgagggtt accgcattca gcgcgacccg     960
atcacgctcc ggccggtcga gcttgattgc ggaccgatca tcgagcccgc tgagtggtat    1020
gagcttcagg cgtggttgga cggcaggggg cgcggcaagg ggcttcccg  ggggcaagcc    1080
attctgtccg ccatggacaa gctgtactgc gagtgtggcg ccgtcatgac ttcgaagcgc    1140
ggggaagaat cgatcaagga ctcttaccgc tgccgtcgcc ggaaggtggt cgacccgtcc    1200
gcacctgggc agcacgaagg cacgtgcaac gtcagcatgg cggcactcga caagttcgtt    1260
gcggaacgca tcttcaacaa gatcaggcac gccgaaggcg acgaagagac gttggcgctt    1320
ctgtgggaag ccgcccgacg cttcggcaag ctcactgagg cgcctgagaa gagcggcgaa    1380
cgggcgaacc ttgttgcgga gcgcgccgac gccctgaacg cccttgaaga gctgtacgaa    1440
gaccgcgcgg caggcgcgta cgacggaccc gttggcagga agcacttccg gaagcaacag    1500
gcagcgctga cgctccggca gcaagggcg  gaagagcggc ttgccgaact gaagccgcc     1560
gaagcccga  agcttcccct tgaccaatgg ttccccgaag acgccgacgc tgacccgacc    1620
ggccctaagt cgtggtgggg cgcgcgtca  gtagacgaca agcgcgtgtt cgtcgggctc    1680
ttcgtagaca agatcgttgt cacgaagtcg actacgggca gggggcaggg aacgcccatc    1740
gagaagcgcg cttcgatcac gtgggcgaag ccgccgaccg acgacgacga agacgacgcc    1800
caggacggca cggaagacgt agcggcgtag tctaga                              1836
```

<210> SEQ ID NO 6
<211> LENGTH: 227
<212> TYPE: DNA
<213> ORGANISM: Artificial Sequence
<220> FEATURE:
<223> OTHER INFORMATION: attP sequence

```
<400> SEQUENCE: 6
ctcgagcaat cgccctgggt gggttacacg acgcccctct atggcccgta ctgacggaca     60
caccgaagcc ccggcggcaa ccctcagcgg atgccccggg gcttcacgtt ttcccaggtc    120
agaagcggtt ttcgggagta gtgccccaac tggggtaacc tttgagttct ctcagttggg    180
ggcgtagggt cgccgacatg acacaagggg ttgtgaccgg gaagctt                  227

<210> SEQ ID NO 7
<211> LENGTH: 2892
<212> TYPE: DNA
<213> ORGANISM: Artificial Sequence
<220> FEATURE:
<223> OTHER INFORMATION: donor vector

<400> SEQUENCE: 7
ccaccgcggt ggcggccgct ctagaactag tggatccccc gggctgcagg aattcgatat     60
caagcttatc gataccgtcg acagatctat aacttcgtat agcatacatt atacgaagtt    120
atgatcaagc tagcttgcta gattttgtat ttcaaatctt gtatatctag gtaagtatat    180
acttagtcaa aatatatgca atagaatctt tgttgtattc ggctcaatcc ttttagtaaa    240
agattgggcc gagtttaatt gcaattcaat taagagaacg aaggataatt acttgagttc    300
tttctcctta tccttcttta tttcctgcta atttatctgc taatgtctac tctagctaca    360
cccgctcaga gaactcgtc aagataggcg atagaaggcg atgcgctgcg aatcgggagc    420
ggcgataccg taaagcacga ggaagcggtc agcccattcg ccgccaagct cttcagcaat    480
atcacgggta gccaacgcta tgtcctgata gcggtccgcc acacccagcc ggccacagtc    540
gatgaatcca gaaaagcggc cattttccac catgatattc ggcaagcagg catcgccatg    600
tgtcacgacg agatcctcgc cgtcgggcat gcgcgccttg agcctggcga acagttcggc    660
tggcgcgagc ccctgatgct cttcgtccag atcatcctga tcgacaagac cggcttccat    720
ccgagtacgt gctcgctcga tgcgatgttt cgcttggtgg tcgaatgggc aggtagccgg    780
atcaagcgta tgcagccgcc gcattgcatc agccatgatg gatactttct cggcaggagc    840
aaggtgagat gacaggagat cctgccccgg cacttcgccc aatagcagcc agtcccttcc    900
cgcttcagtg acaacgtcga gcacagctgc gcaaggaacg cccgtcgtgg ccagccacga    960
tagccgcgct gcctcgtcct ggagttcatt cagggcaccg gacaggtcgg tcttgacaaa   1020
aagaaccggg cgcccctgcg ctgacagccg gaacacggcg gcatcagagc agccgattgt   1080
ctgttgtgcc cagtcatagc cgaatagcct ctccacccaa gcggccggag aacctgcgtg   1140
caatccatct tgttcaatgc tagccgtgga accccagaa ccagaagtag taggattgat   1200
tctcataata ataaaataaa taatatgtc gaaatgtttt tgcaaaaatt atcgaatta    1260
aaataaatgt ccgcttgcac gtcgatcggt taattctccc agaaatatag ccatccctgc   1320
cccctcacgt caatcccacg agcctcttat ccattctcat tgaacgacgg cggggagcg   1380
agcttcccgg tcacaacccc ttgtgtcatg tcggcgaccc tacgccccca actgagagaa   1440
ctcaaaggtt accccagttg gggcactact cccgaaaacc gcttctgacc tgggaaaacg   1500
tgaagccccg gggcatccgc tgagggttgc cgccggggct tcggtgtgtc cgtcagtacg   1560
ggccatagag gggcgtcgtg taacccaccc agggcgattg ctcgaccagc ttttgttccc   1620
tttagtgagg gttaattgcg cgcttggcgt aatcatggtc atagctgttt cctgtgtgaa   1680
attgttatcc gctcacaatt ccacacaaca tacgagccgg aagcataaag tgtaaagcct   1740
ggggtgccta atgagtgagc taactcacat taattgcgtt gcgctcactg cccgctttcc   1800
```

-continued

```
agtcgggaaa cctgtcgtgc cagctgcatt aatgaatcgg ccaacgcgcg gggagaggcg      1860
gtttgcgtat tgggcgctct tccgcttcct cgctcactga ctcgctgcgc tcggtcgttc      1920
ggctgcggcg agcggtatca gctcactcaa aggcggtaat acggttatcc acagaatcag      1980
gggataacgc aggaaagaac atgtgagcaa aaggccagca aaaggccagg aaccgtaaaa      2040
aggccgcgtt gctggcgttt ttccataggc tccgcccccc tgacgagcat cacaaaaatc      2100
gacgctcaag tcagaggtgg cgaaacccga caggactata aagataccag gcgtttcccc      2160
ctggaagctc cctcgtgcgc tctcctgttc cgaccctgcc gcttaccgga tacctgtccg      2220
cctttctccc ttcgggaagc gtggcgcttt ctcatagctc acgctgtagg tatctcagtt      2280
cggtgtaggt cgttcgctcc aagctgggct gtgtgcacga acccccegtt cagcccgacc      2340 gctgcgcctt atccggtaac tatcgtcttg agtccaaccc ggtaagacac gacttatcgc      2400
cactggcagc agccactggt aacaggatta gcagagcgag gtatgtaggc ggtgctacag      2460
agttcttgaa gtggtggcct aactacggct acactagaag gacagtattt ggtatctgcg      2520
ctctgctgaa gccagttacc ttcggaaaaa gagttggtag ctcttgatcc ggcaaacaaa      2580
ccaccgctgg tagcggtggt ttttttgttt gcaagcagca gattacgcgc agaaaaaaag      2640
gatctcaaga agatccttttg atcttttcta cggggtctga cgctcagtgg aacgaaaact      2700
cacgttaagg gattttggtc atgagattat caaaaaggat cttcacctag atccttttaa      2760
attaaaaatg aagttttaaa tcaatctaaa gtatatatga gtaaacttgg tctgacagtt      2820
accaatgctt aatcagtgag gcacctatct cagcgatctg tctatttcgt tcatccatag      2880
ttgcctgact cc                                                         2892
```

<210> SEQ ID NO 8  
<211> LENGTH: 89  
<212> TYPE: DNA  
<213> ORGANISM: Artificial Sequence  
<220> FEATURE:  
<223> OTHER INFORMATION: attL sequence

<400> SEQUENCE: 8

```
agccgcggtg cgggtgccag ggcgtgccct tgagttctct cagttggggg cgtagggtcg       60
ccgacatgac acaagggggtt gtgaccggg                                        89
```

<210> SEQ ID NO 9  
<211> LENGTH: 184  
<212> TYPE: DNA  
<213> ORGANISM: Artificial Sequence  
<220> FEATURE:  
<223> OTHER INFORMATION: attR sequence

<400> SEQUENCE: 9

```
gagcaatcgc cctgggtggg ttacacgacg cccctctatg gcccgtactg acggacacac       60
cgaagccccg gcggcaaccc tcagcggatg ccccggggct tcacgttttc ccaggtcaga      120
agcggttttc gggagtagtg ccccaactgg ggtaacccttt gggctccccg ggcgcgtact      180
ccac                                                                   184
```

<210> SEQ ID NO 10  
<211> LENGTH: 46  
<212> TYPE: DNA  
<213> ORGANISM: Artificial Sequence  
<220> FEATURE:  
<223> OTHER INFORMATION: complementary oligonucleotide

```
<400> SEQUENCE: 10
ggtaccataa cttcgtataa tgtatgctat acgaagttat agatct                              46

<210> SEQ ID NO 11
<211> LENGTH: 46
<212> TYPE: DNA
<213> ORGANISM: Artificial Sequence
<220> FEATURE:
<223> OTHER INFORMATION: complementary oligonucleotide

<400> SEQUENCE: 11
agatctataa cttcgtatag catacattat acgaagttat ggtacc                              46

<210> SEQ ID NO 12
<211> LENGTH: 46
<212> TYPE: DNA
<213> ORGANISM: Artificial Sequence
<220> FEATURE:
<223> OTHER INFORMATION: complementary oligonucleotide

<400> SEQUENCE: 12
agatctataa cttcgtataa tgtatgctat acgaagttat aagctt                              46

<210> SEQ ID NO 13
<211> LENGTH: 46
<212> TYPE: DNA
<213> ORGANISM: Artificial Sequence
<220> FEATURE:
<223> OTHER INFORMATION: complementary oligonucleotide

<400> SEQUENCE: 13
aagcttataa cttcgtatag catacattat acgaagttat agatct                              46

<210> SEQ ID NO 14
<211> LENGTH: 63
<212> TYPE: DNA
<213> ORGANISM: Artificial Sequence
<220> FEATURE:
<223> OTHER INFORMATION: complementary oligonucleotide

<400> SEQUENCE: 14
ctgcagccgc ggtgcgggtg ccagggcgtg cccttgggct ccccgggcgc gtactccact              60
agt                                                                             63

<210> SEQ ID NO 15
<211> LENGTH: 63
<212> TYPE: DNA
<213> ORGANISM: Artificial Sequence
<220> FEATURE:
<223> OTHER INFORMATION: complementary oligonucleotide

<400> SEQUENCE: 15
actagtggag tacgcgcccg gggagcccaa gggcacgccc tggcacccgc accgcggctg              60
cag                                                                             63

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
caactcgagc aatcgccctg ggtg                                                      24
```

```
<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
caaaagcttc ccggtcacaa ccccttg                                       27

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ccgccagcgt tcatcctgag c                                             21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
tgacagccgg aacacggcgg c                                             21

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tgaagagctt ggcggcgaat                                               20

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
gagatgtaac tccagttcc                                                19

<210> SEQ ID NO 22
<211> LENGTH: 48
<212> TYPE: DNA
<213> ORGANISM: Artificial Sequence
<220> FEATURE:
<223> OTHER INFORMATION: linker sequence

<400> SEQUENCE: 22
gaacttgttg aaggaaaatt ggagctagta gaaggtctta aagtcgcc                48

<210> SEQ ID NO 23
<211> LENGTH: 30
<212> TYPE: DNA
<213> ORGANISM: Artificial Sequence
<220> FEATURE:
<223> OTHER INFORMATION: linker sequence
```

```
<400> SEQUENCE: 23
gaacttgcag ttgaaggaaa attggaggcc                                              30

<210> SEQ ID NO 24
<211> LENGTH: 1041
<212> TYPE: DNA
<213> ORGANISM: E. coli

<400> SEQUENCE: 24
ccatggctag caaaaagcct gaactcaccg cgacgtctgt cgagaagttt ctgatcgaaa            60
agttcgacag cgtctccgac ctgatgcagc tctcggaggg cgaagaatct cgtgctttca          120
gcttcgatgt aggagggcgt ggatatgtcc tgcgggtaaa tagctgcgcc gatggttct            180 acaaagatcg ttatgtttat cggcactttg catcggccgc gctcccgatt ccggaagtgc          240
ttgacattgg ggaatttagc gagagcctga cctattgcat ctcccgccgt gcacagggtg          300
tcacgttgca agacctgcct gaaaccgaac tgcccgctgt tctgcagccg gtcgcggagg          360
ctatggatgc gatcgctgcg gccgatctta gccagacgag cgggttcggc ccattcggac          420
cgcaaggaat cggtcaatac actacatggc gtgatttcat atgcgcgatt gctgatcccc          480
atgtgtatca ctggcaaact gtgatggacg acaccgtcag tgcgtccgtc gcgcaggctc          540
tcgatgagct gatgctttgg gccgaggact gccccgaagt ccggcacctc gtgcacgcgg          600
atttcggctc caacaatgtc ctgacggaca atggccgcat aacagcggtc attgactgga          660
gcgaggcgat gttcggggat tcccaatacg aggtcgccaa catcttcttc tggaggccgt          720
ggttggcttg tatggagcag cagacgcgct acttcgagcg gaggcatccg gagcttgcag          780
gatcgccgcg gctccgggcg tatatgctcc gcattggtct tgaccaactc tatcagagct          840
tggttgacgg caatttcgat gatgcagctt gggcgcaggg tcgatgcgac gcaatcgtcc          900
gatccggagc cgggactgtc gggcgtacac aaatcgcccg cagaagcgcg gccgtctgga          960
ccgatggctg tgtagaagta ctcgccgata gtggaaaccg acgccccagc actcgtcctc         1020
gagcaaagga atagatctag a                                                   1041

<210> SEQ ID NO 25
<211> LENGTH: 2391
<212> TYPE: DNA
<213> ORGANISM: Artificial Sequence
<220> FEATURE:
<223> OTHER INFORMATION: plasmid fragment

<400> SEQUENCE: 25
gagctcggta ccgctccccc gccgtcgttc aatgagaatg gataagaggc tcgtgggatt           60
gacgtgaggg ggcagggatg gctatatttc tgggagcgaa ctccgggcga attcgaagcg         120
cttggataca gttgtaggga gggatccatg ctagcgaca cgtacgcggg tgcttacgac          180
cgtcagtcgc gcgagcgcga aaattcgagc gcagcaagcc cagcgacaca gcgtagcgcc         240
aacgaagaca aggcggccga ccttcagcgc gaagtcgagc gcgacggggg ccggttcagg         300
ttcgtcgggc atttcagcga agcgccgggc acgtcggcgt cgggacggc ggagcgcccg          360 gagttcgaac gcatcctgaa cgaatgccgc gccgggcggc tcaacatgat cattgtctat         420
gacgtgtcgc gcttctcgcg cctgaaggtc atggacgcga ttccgattgt ctcggaattg         480
ctcgccctgg gcgtgacgat tgtttccact caggaaggcg tcttccggca gggaaacgtc         540 atggaccctga ttcacctgat tatgcggctc gacgcgtcgc acaaagaatc ttcgctgaag         600
tcggcgaaga ttctcgacac gaagaacctt cagcgcgaat gggcgggta cgtcggcggg         660
```

```
aaggcgcctt acggcttcga gcttgtttcg gagacgaagg agatcacgcg caacggccga      720
atggtcaatg tcgtcatcaa caagcttgcg cactcgacca ctcccttac cggacccttc       780 gagttcgagc ccgacgtaat ccggtggtgg tggcgtgaga tcaagacgca caaacacctt      840
cccttcaagc cgggcagtca agccgccatt cacccgggca gcatcacggg gctttgtaag      900
cgcatggacg ctgacgccgt gccgacccgg ggcgagacga ttgggaagaa gaccgcttca      960
agcgcctggg acccggcaac cgttatgcga atccttcggg acccgcgtat tgcgggcttc     1020
gccgctgagg tgatctacaa gaagaagccg gacggcacgc cgaccacgaa gattgagggt     1080
taccgcattc agcgcgaccc gatcacgctc cggccggtcg agcttgattg cggaccgatc     1140
atcgagcccg ctgagtggta tgagcttcag gcgtggttgg acggcagggg gcgcggcaag     1200
gggctttccc gggggcaagc cattctgtcc gccatggaca gctgtactg cgagtgtggc      1260 gccgtcatga cttcgaagcg cggggaagaa tcgatcaagg actcttaccg ctgccgtcgc     1320
cggaaggtgg tcgacccgtc cgcacctggg cagcacgaag gcacgtgcaa cgtcagcatg     1380
gcggcactcg acaagttcgt tgcggaacgc atcttcaaca agatcaggca cgccgaaggc     1440
gacgaagaga cgttggcgct tctgtgggaa gccgccgac gcttcggcaa gctcactgag      1500
gcgcctgaga agagcggcga acgggcgaac cttgttgcgg agcgcgccga cgccctgaac     1560
gcccttgaag agctgtacga agaccgcgcg gcaggcgcgt acgacggacc cgttggcagg     1620
aagcacttcc ggaagcaaca ggcagcgctg acgctccggc agcaagggc ggaagagcgg      1680 cttgccgaac ttgaagccgc cgaagccccg aagcttcccc ttgaccaatg gttccccgaa     1740
gacgccgacg ctgacccgac cggccctaag tcgtggtggg ggcgcgcgtc agtagacgac     1800
aagcgcgtgt tcgtcgggct cttcgtagac aagatcgttg tcacgaagtc gactacgggc     1860
agggggcagg gaacgcccat cgagaagcgc gcttcgatca cgtgggcgaa gccgccgacc     1920
gacgacgacg aagacgacgc ccaggacggc acggaagacg tagcggcgta gtctagagcg     1980
atcctggcct agtctatagg aggttttgaa agaaaggag caataatcat tttcttgttc      2040
tatcaagagg gtgctattgc tccttttctt ttttcttttt atttatttac tagtatttta     2100
cttacataga cttttttgtt tacattatag aaaaagaagg agaggttatt ttcttgcatt     2160
tattcatgat tgagtattct attttgattt tgtatttgtt taaattgtga aatagaactt     2220
gtttctcttc ttgctaatgt tactatatct ttttgatttt ttttttccaa aaaaaaaatc     2280 aaatttgac ttcttcttat ctcttatctt tgaatatctc ttatctttga aataataata     2340
tcattgaaat aagaaagaag agctatattc gacctgcagg catgcaagct t              2391
```

<210> SEQ ID NO 26
<211> LENGTH: 2145
<212> TYPE: DNA
<213> ORGANISM: Artificial Sequence
<220> FEATURE:
<223> OTHER INFORMATION: plasmid fragment

<400> SEQUENCE: 26

```
gagctcggta cccaaagctc ccccgccgtc gttcaatgag aatggataag aggctcgtgg       60
gattgacgtg agggggcagg gatggctata tttctgggag cgaactccgg gcgaatacga      120
agcgcttgga tacagttgta gggagggatc catggctagc gacacgtacg cgggtgctta     180
cgaccgtcag tcgcgcgagc gcgaaaattc gagcgcagca agcccagcga cacagcgtag     240
cgccaacgaa gacaaggcgg ccgaccttca gcgcgaagtc gagcgcgacg ggggccggtt     300
caggttcgtc gggcatttca gcgaagcgcc gggcacgtcg gcgttcggga cggcggagcg     360
```

| | |
|---|---|
| cccggagttc gaacgcatcc tgaacgaatg ccgcgccggg cggctcaaca tgatcattgt | 420 |
| ctatgacgtg tcgcgcttct cgcgcctgaa ggtcatggac gcgattccga ttgtctcgga | 480 |
| attgctcgcc ctgggcgtga cgattgtttc cactcaggaa ggcgtcttcc ggcagggaaa | 540 |
| cgtcatggac ctgattcacc tgattatgcg gctcgacgcg tcgcacaaag aatcttcgct | 600 |
| gaagtcggcg aagattctcg acacgaagaa ccttcagcgc gaattgggcg gtacgtcgg | 660 |
| cgggaaggcg ccttacggct tcgagcttgt ttcggagacg aaggagatca cgcgcaacgg | 720 |
| ccgaatggtc aatgtcgtca tcaacaagct tgcgcactcg accactcccc ttaccggacc | 780 |
| cttcgagttc gagcccgacg taatccggtg gtggtggcgt gagatcaaga cgcacaaaca | 840 |
| ccttcccttc aagccgggca gtcaagccgc cattcacccg ggcagcatca cggggctttg | 900 |
| taagcgcatg gacgctgacg ccgtgccgac ccggggcgag acgattggga agaagaccgc | 960 |
| ttcaagcgcc tgggacccgg caaccgttat gcgaatcctt cgggacccgc gtattgcggg | 1020 |
| cttcgccgct gaggtgatct acaagaagaa gccgacggc acgccgacca cgaagattga | 1080 |
| gggttaccgc attcagcgcg acccgatcac gctccggccg gtcgagcttg attgcggacc | 1140 |
| gatcatcgag cccgctgagt ggtatgagct caggcgtgg ttggacggca gggggcgcgg | 1200 |
| caagggcgtt tcccgggggc aagccattct gtccgccatg acaagctgt actgcgagtg | 1260 |
| tggcgccgtc atgacttcga agcgcgggga agaatcgatc aaggactctt accgctgccg | 1320 |
| tcgccggaag gtggtcgacc cgtccgcacc tgggcagcac gaaggcacgt gcaacgtcag | 1380 |
| catgcgcgga ctcgacaagt tcgttgcgga acgcatcttc aacaagatca ggcacgccga | 1440 |
| aggcgacgaa gagacgttgg cgcttctgtg ggaagccgcc cgacgcttcg gcaagctcac | 1500 |
| tgaggcgcct gagaagagcg gcgaacgggc gaaccttgtt gcggagcgcg ccgacgccct | 1560 |
| gaacgccctt gaagagctgt acgaagaccg cgcggcaggc gcgtacgacg acccgttgg | 1620 |
| caggaagcac ttccggaagc aacaggcagc gctgacgctc cggcagcaag gggcggaaga | 1680 |
| gcggcttgcc gaacttgaag ccgccgaagc cccgaagctt ccccttgacc aatggttccc | 1740 |
| cgaagacgcc gacgctgacc cgaccggcc taagtcgtgg tggggcgcg cgtcagtaga | 1800 |
| cgacaagcgc gtgttcgtcg ggctcttcgt agacaagatc gttgtcacga agtcgactac | 1860 |
| gggcaggggg cagggaacgc ccatcgagaa gcgcgcttcg atcacgtggg cgaagccgcc | 1920 |
| gaccgacgac gacgaagacg acgcccagga cggcacggaa gacgtagcgg cgtagtctag | 1980 |
| agaaattcaa ttaaggaaat aaattaagga aatacaaaaa gggggggtagt catttgtata | 2040 |
| taactttgta tgactttct cttctatttt tttgtatttc ctcccttcc tttctattt | 2100 |
| gtattttttt atcattgctt ccattgaatt aattcatgca agctt | 2145 |

<210> SEQ ID NO 27
<211> LENGTH: 2871
<212> TYPE: DNA
<213> ORGANISM: Artificial Sequence
<220> FEATURE:
<223> OTHER INFORMATION: plasmid fragment

<400> SEQUENCE: 27

| | |
|---|---|
| gaattcattt tcacgtgtgg aagatatgaa ttttttttgag aaactagata agattaatga | 60 |
| atatcggtgt tttggttttt tcttgtggcc gtctttgttt atattgagat ttttcaaatc | 120 |
| agtgcgcaag acgtgacgta agtatctgag ctagttttta ttttctact aatttggtcg | 180 |
| tttatttcgg cgtgtaggac atggcaaccg ggcctgaatt tcgcgggtat tctgtttcta | 240 |
| ttccaacttt ttcttgatcc gcagccatta acgactttg aatagatacg ctgacacgcc | 300 |

-continued

```
aagcctcgct agtcaaaagt gtaccaaaca acgctttaca gcaagaacgg aatgcgcgtg    360
acgctcgcgg tgacgccatt tcgccttttc agaaatggat aaatagcctt gcttcctatt    420
atatcttccc aaattaccaa tacattacac tagcatctga atttcataac caatctcgat    480
acaccaaatc gataggatcc aattcaacca caagaactaa caaagtcaga aaaatggctt    540
ctatgatatc ctcttccgct gtgacaacag tcagccgtgc ttctagggtg caatccgcgg    600
cagtggctcc attcggcggc tgaaatcca tgactggatt cccagtgaag aaggtcaaca     660
ctgacattac ttccattaca agcaatggtg aagagtaaa gtgcatgcag gtgtggcctc     720
caattggaaa gaagaagttt gagactcttt cctatttgcc accattgacc atggctagcg    780
acacgtacgc gggtgcttac gaccgtcagt cgcgcgagcg cgagaattcg agcgcagcaa    840
gcccagcgac acagcgtagc gccaacgaag acaaggcggc cgaccttcag cgcgaagtcg    900
agcgcgacgg gggccggttc aggttcgtcg ggcatttcag cgaagcgccg ggcacgtcgg    960
cgttcgggac ggcggagcgc ccggagttcg aacgcatcct gaacgaatgc cgcgccgggc   1020
ggctcaacat gatcattgtc tatgacgtgt cgcgcttctc gcgcctgaag gtcatggacg   1080
cgattccgat tgtctcggaa ttgctcgccc tgggcgtgac gattgtttcc actcaggaag   1140
gcgtcttccg gcagggaaac gtcatggacc tgattcacct gattatgcgg ctcgacgcgt   1200
cgcacaaaga atcttcgctg aagtcggcga agattctcga cacgaagaac cttcagcgcg   1260
aattgggcgg gtacgtcggc gggaaggcgc cttacggctt cgagcttgtt tcggagacga   1320
aggagatcac gcgcaacggc cgaatggtca atgtcgtcat caacaagctt gcgcactcga   1380
ccactcccct taccggaccc ttcgagttcg agcccgacgt aatccggtgg tggtggcgtg   1440
agatcaagac gcacaaacac cttcccttca agccgggcag tcaagccgcc attcacccgg   1500
gcagcatcac ggggctttgt aagcgcatgg acgctgacgc cgtgccgacc cggggcgaga   1560
cgattgggaa gaagaccgct tcaagcgcct gggacccggc aaccgttatg cgaatccttc   1620
gggacccgcg tattgcgggc ttcgccgctg aggtgatcta caagaagaag ccggacggca   1680
cgccgaccac gaagattgag ggttaccgca ttcagcgcga cccgatcacg ctccggccgg   1740
tcgagcttga ttgcggaccg atcatcgagc ccgctgagtg gtatgagctt caggcgtggt   1800
tggacggcag ggggcgcggc aagggggcttt cccgggggca agccattctg tccgccatgg   1860
acaagctgta ctgcgagtgt ggcgccgtca tgacttcgaa gcgcggggaa gaatcgatca   1920
aggactctta ccgctgccgt cgccggaagg tggtcgaccc gtccgcacct gggcagcacg   1980
aaggcacgtg caacgtcagc atggcggcac tcgacaagtt cgttgcggaa cgcatcttca   2040
acaagatcag gcacgccgaa ggcgacgaag agacgttggc gcttctgtgg gaagccgccc   2100
gacgcttcgg caagctcact gaggcgcctg agaagagcgg cgaacgggcg aaccttgttg   2160
cggagcgcgc cgacgccctg aacgcccttg aagagctgta cgaagaccgc gcggcaggcg   2220
cgtacgacgg acccgttggc aggaagcact tccggaagca acaggcagcg ctgacgctcc   2280
ggcagcaagg ggcggaagag cggcttgccg aacttgaagc cgccgaagcc ccgaagcttc   2340
cccttgacca atggttcccc gaagacgccg acgctgaccc gaccggccct aagtcgtggt   2400
gggggcgcgc gtcagtagac gacaagcgcg tgttcgtcgg gctcttcgta gacaagatcg   2460
ttgtcacgaa gtcgactacg ggcaggggc agggaacgcc catcgagaag cgcgcttcga   2520
tcacgtgggc gaagccgccg accgacgacg acgaagacga cgcccaggac ggcacggaag   2580
acgtagcggc gtagtctaga gtcgaagcag atcgttcaaa catttggcaa taaagtttct   2640
taagattgaa tcctgttgcc ggtcttgcga tgattatcat ataatttctg ttgaattacg   2700
```

```
ttaagcatgt aataattaac atgtaatgca tgacgttatt tatgagatgg gtttttatga    2760
ttagagtccc gcaattatac atttaatacg cgatagaaaa caaaatatag cgcgcaaact    2820
aggataaatt atcgcgcgcg gtgtcatcta tgttactaga tcgacctgca g             2871
```

<210> SEQ ID NO 28
<211> LENGTH: 16
<212> TYPE: PRT
<213> ORGANISM: Artificial Sequence
<220> FEATURE:
<223> OTHER INFORMATION: linker sequence

<400> SEQUENCE: 28

```
Glu Leu Val Glu Gly Lys Leu Glu Leu Val Glu Gly Leu Lys Val Ala
 1               5                  10                  15
```

<210> SEQ ID NO 29
<211> LENGTH: 10
<212> TYPE: PRT
<213> ORGANISM: Artificial Sequence
<220> FEATURE:
<223> OTHER INFORMATION: linker sequence

<400> SEQUENCE: 29

```
Glu Leu Ala Val Glu Gly Lys Leu Glu Ala
 1               5                  10
```

TRANSGENIC PLANTS HAVING TRANSFORMED PLASTID GENOMES AND PROGENY THEREOF

This application is a §371 application of PCT/US02/09537 filed Mar. 29, 2002, which in turn claims priority to U.S. Provisional Application 60/279,615 filed Mar. 29, 2001. The entire disclosure of each of the above-identified applications is incorporated herein by reference.

FIELD OF THE INVENTION

This invention is related to the fields of molecular biology and transgenic plants. More specifically, the present invention provides compositions and methods which facilitate the insertion and excision of transgenes from the plastids of higher plants.

BACKGROUND OF THE INVENTION

Several publications and patent documents are referenced in this application by numerals in parentheses in order to more fully describe the state of the art to which this invention pertains. The disclosure of each of these publications and patent documents is incorporated by reference herein.

The plastid genome of higher plants is a circular double-stranded DNA molecule, 120-160 kb in size, which may be present in 1900-50000 copies per leaf cell, which carries about 100 chloroplasts (Bendich 1987; Sugiura 1992). There are several reasons why incorporation of transgenes in the plastid genome may be preferred over incorporation of transgenes into the nuclear genome. The advantages of plastid transformation include: natural containment due to lack of pollen transmission in most crops; high-level protein expression; feasibility of expressing multiple genes from operons; and lack of position effect (Maliga 1993; Maliga et al. 1993; Heifetz 2000; Bock 2001; Heifetz and Tuttle 2001; Maliga 2002). Useful traits expressed in chloroplasts are the *Bacillus thuringiensis* insecticidal protein (McBride et al. 1995; Kota et al. 1999), herbicide resistance (Daniell et al. 1998; Lutz et al. 2001; Ye et al. 2001) and expression of human somatotropin (Staub et al. 2000).

For almost a decade, plastid transformation was feasible only in tobacco (*Nicotiana tabacum*). Plastid transformation has recently been extended to *Arabidopsis thaliana* (Sikdar et al. 1998), potato (*Solanum tuberosum*) (Sidorov et al. 1999), tomato (Ruf et al. 2001) and progress has been made towards transforming plastids in rice (Khan and Maliga 1999). Plastid transformation in these new species has been very inefficient as compared to tobacco. Clearly, a need exists for improved compositions and methods for expressing transgenes in the plastids of a wider range of higher plant species.

SUMMARY OF THE INVENTION

In accordance with the present invention compositions and methods are provided for catalyzing insertion of heterologous nucleic acid sequences into the genome of higher plants. One exemplary method comprises i) providing a recipient plant having a transformed plastid genome which contains a first recombination site; ii) introducing an integrase into the recipient plant and further introducing a heterologous DNA construct comprising a second recombination site, a sequence encoding a gene of interest and optionally a selectable marker gene into the plant, wherein the integrase acts on the first and second recombination sites and catalyzes the insertion of the sequence encoding the gene of interest into the plastid genome.

In a preferred embodiment, the first and second recombination sites are interchangeably referred to as attB and attP sites and the integrase is a phiC31 integrase.

The integrase may be stably or transiently expressed in the target plant. Methods and compositions for effecting stable or transient expression are provided herein.

In accordance with the present invention, endogenous recombination sites within the plastid genome have been discovered. Accordingly, a further method of the invention comprises catalyzing insertion of heterologous nucleic acid sequences encoding a gene of interest utilizing an integrase that acts on at least one endogenous recombination site.

In certain embodiments, selectable marker genes are utilized to identify transformed plants. In cases where it is desirable to excise such selectable marker genes, the methods of the invention encompass the use of the CRE-LOX system to eliminate sequences from the transgenic plants of the invention.

In yet another aspect, plasmids are provided with facilitate practicing the methods of the present invention.

Also encompassed within the scope of the invention are plants and progeny plants transformed using the methods disclosed.

BRIEF DESCRIPTION OF THE DRAWINGS

FIG. 10 shows (A) a partial map of the Nt-pSAC114 plastid genome after integration of donor vector pKO103. INT function was provided transiently by plasmids pKO107 or pKO111. PCR primer positions and the predicted size of junction fragments are shown. Plastid genes rrn16, trnV, rps12/7, aadA (flanked by direct lox sites), the attL sequence, the neo gene, a third lox site, an attR sequence and the relevant restriction sites are marked. (B) PCR amplification of attL and attR junctions.

FIG. 14 is an experimental design of System 2B for integration of foreign DNA mediated by expressing a plastid encoded INT from a dicistronic operon. Shown are (A) the plastid genome containing one lox site, a dicistronic int-aadA gene including a promoter (P1), editing segment (Ed), int coding region, RBS, aadA coding region and terminator (T1). (B) The donor vector carries an attP site, a neo gene, ColE1 ori, lox site and a gene of interest (goi). (C) The plastid genome after integrase mediated insertion of donor vector. attL and attR sequences were generated by INT mediated attB-attP recombination. (D) The plastid genome after CRE mediated deletion of the chimeric int-aadA gene, the attL site and the neo gene.

FIG. 18 is a schematic design for INT mediated integration of bar. Shown are (A) the plastid genome containing a P1 promoter, a lox site, a RBS and a marker coding region with a T1 terminator, a second lox site in direct orientation with the first lox site and an attB site. This plastid genome is the progenitor of the recipient line. (B) The recipient plastid genome obtained by excision of the marker gene (mg) by CRE. (C) Donor vector with dicistronic bar operon has an attP site, ColE1 ori, P2 promoter, a marker coding region, one lox site, a RBS and a bar coding region with a T1 terminator. (D) Donor vector with promoter-less dicistronic bar operon consists of an attP site, ColE1 ori, RBS, a marker coding region, lox site, RBS, and a bar coding region with a T1 terminator. (E) The plastid genome after INT mediated insertion of donor vector with dicistronic bar operon (FIG. 18C above). attL and attR sequences were generated by INT mediated attB-attP recombination. (F) The plastid genome after INT mediated insertion of donor vector with promoter-less dicistronic bar operon shown in FIG. 18D. attL and attR sequences were generated by INT mediated attB-attP recombination. (G) The plastid genome after CRE mediated excision of the attL and marker gene sequences from the plastid genomes shown in FIG. 18E and FIG. 18F.

FIG. 19 is a schematic design for marker gene excision by a transiently expressed CRE. Shown are (A) the recipient plastid genome with lox and attB sites. INT is provided transiently from a plastid or nuclear gene. (B) Donor vector with attP, ColE1 ori, a P1:aadA:codA:T1 fusion, a lox site, and a goi. (C) The plastid genome obtained after INT mediated insertion of donor vector. (D) The plastid genome after transient CRE mediated excision of the attL sequence and the fused (aadA:codA) marker gene.

DETAILED DESCRIPTION OF THE INVENTION

Figure 1B:
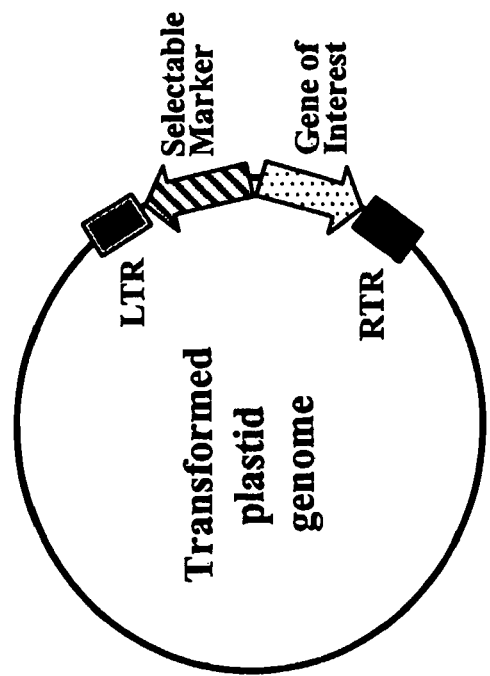
FIG. 1 shows a schematic of transformation of the plastid genome which is formed by two recombination events via homologous targeting sequences. Plastid genome segments included in vector are marked as left and right targeting regions (LTR, RTR), respectively.

The following definitions are provided to facilitate an understanding of the present invention.

Heteroplastomic refers to the presence of a mixed population of different plastid genomes within a single plastid or in a population of plastids contained in plant cells or tissues.

Homoplastomic refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome refers to the genome of a plastid.

Transplastome refers to a transformed plastid genome.

Transformation of plastids refers to the stable integration of transforming DNA into the plastid genome that is transmitted to the seed progeny of plants containing the transformed plastids.

Selectable marker gene refers to a gene or a nucleic acid sequence that upon expression confers a phenotype by which successfully transformed plastids or cells or tissues carrying the transformed plastid can be identified. One class of exemplary selectable marker genes comprises antibiotic or herbicide resistance genes. Another class of marker does not confer resistance but enables visual screening of transformed plant cells. Such markers include, without limitation, green fluorescent proteins.

Transforming DNA refers to homologous DNA, or a heterologous DNA flanked by homologous DNA, which when introduced into plastids becomes part of the plastid genome by homologous recombination. In this type of transformation, a sufficient degree of homology between the homologous tranforming DNA and the targeted plastid genome is all that is required for insertion of the transforming DNA into the plastid genome.

An alternative type of transforming DNA refers to a DNA which contains recombination site sequences for a site-specific recombinase or integrase. Insertion of this type of DNA is not dependent of the degree of homology between the transforming DNA and the plastid to be transformed but rather is catalyzed by the action of the recombinase or integrase on the first and second recombination sites.

Recombination sites as used herein refers to specific polynucleotide sequences that are recognized by the recombinase or integrase enzymes described herein. Typically, two different sites are involved, one present in the target nucleic acid and another on the nucleic acid that is to be integrated at the target recombination site. The terms attB and attP attachment sites originally from a bacterial target and a phage donor, respectively, are used herein although recombination sites for particular enzymes may have different names.

Operably linked refers to two different regions or two separate genes spliced together in a construct such that both regions will function to promote gene expression and/or protein translation.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

A "clone" or "clonal cell population" is a population of cells derived from a single cell or common ancestor by mitosis.

A "cell line" is a clone of a primary cell or cell population that is capable of stable growth in vitro for many generations.

Figure 1A:
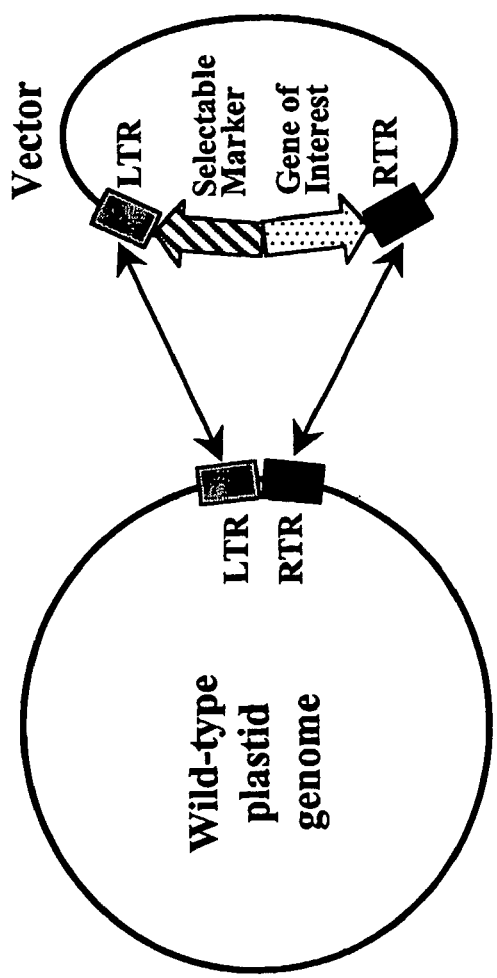

Stable transformation of the tobacco plastid genome is achieved in tobacco leaves using the biolistic method for DNA delivery. The foreign heterologous DNA integrates into the plastid genome by homologous recombination via the left and right targeting regions of the plastid transformation vector (FIG. 1). The targeting regions are derived from the plastid genome. The insertion site is selected so that the transgene does not interfere with the expression of the flanking plastid genes. The heterologous DNA segment typically contains a selectable marker gene and a gene of interest (goi) with no selectable phenotype. Expression of the antibiotic resistance gene confers a selective advantage to the chloroplast, which gradually replaces the plastids lacking the antibiotic resistance gene. The homoplastomic state is obtained when all the plastid genome (plastome) copies are transformed, which takes about 20 cell generations (Moll et al. 1990). The sorting out process takes place while the leaf segment is cultured on an antibiotic containing shoot regeneration medium. The shoots regenerated on the selective medium are typically chimeric, containing sectors with transformed and wild type plastid genome copies. Genetically stable, homoplastomic plants are obtained by shoot regeneration from transformed leaf sectors. In an exemplary protocol, leaf tissue is targeted for biolistic DNA delivery of heterologous DNA comprising homologous DNA recombining segments and nucleic acid sequences encoding spectinomycin resistance as a selective marker. In an alternative embodiment of this method, spectinomycin resistance conferred by insertion of sequences encoding a mutant plastid 16S ribosomal RNA gene (Svab et al. 1990; Staub and Maliga 1993). In yet another embodiment, spectinomycin resistance was conferred by the more efficient bacterial aadA gene (Svab and Maliga 1993). Streptomycin resistance was carried by both vector systems, but spectinomycin resistance was used as a primary means of selection. The pPRV (plastid repeat vector) plasmids are a plastid vector series with convenient restriction sites at the insertion site with no significant read-through transcription (Zoubenko et al. 1994). A variant of this plastid transformation method was reported from three European laboratories which utilize PEG treatment of protoplasts as a method of DNA introduction (Golds et al. 1993; O'Neill et al. 1993; Koop et al. 1996).

An alternative approach to plastid transformation has been attempted by Dr. Henry Daniell and colleagues who built a vector system designed to function as an independent replicon and utilized chloramphenicol resistance as a selectable marker (Daniell 1993). No stable maintenance of these vectors in chloroplasts or selection of plastid transformation events by chloramphenicol resistance was reported.

Perceiving DNA delivery as the bottleneck of plastid transformation, a sophisticated chloroplast microinjection protocol has recently been developed. Thus far the system has been used only to demonstrate transient expression of the microinjected DNA (Knoblauch et al. 1999).

It appears that there are two issues of importance for general applicability of plastid transformation.

1) Choice and expression level of selectable marker genes. The protocols for non-tobacco species have utilized aadA as the selectable marker encoding aminoglycoside 3"-adenyltransferase and selection for resistance to spectinomycin (potato, tomato, Arabidopsis) or streptomycin (rice) which are rendered inactive by adenylation. Both spectinomycin and streptomycin inhibit protein synthesis on prokaryotic-type ribosomes. Interestingly, most other inhibitors of protein synthesis on prokaryotic-type ribosomes (for example gentamycin, hygromycin) have been shown to be unsuitable for selection of plastid transformation events, although they make the cells resistant once the antibiotic inactivating gene is present in all plastid genome copies. The same is true for the bar gene that confers PPT resistance when present in all plastid genome copies, but is not suitable for direct selection of transplastomic clones (Lutz et al. 2001). This observation suggested that increasing the output of gene product per marker gene copy should improve the performance of the marker genes. Indeed, kanamycin resistance, which in the past was considered to be an inefficient marker (Carrer et al. 1993) was improved 10-fold by expressing the neo gene at a higher level. The efficiency of selection with the new kanamycin-resistance (neo) genes and the spectinomycin resistance (aadA) genes is now comparable. Also, we attribute successful plastid transformation in rice to high-level expression of the aadA gene (Khan and Maliga 1999). High level expression may be important during the early stage of plastid transformation when only a few of the thousands of genome copies are transformed. However, accumulation of the marker gene product at 10% to 20% of total soluble protein is unacceptable when all the genome copies are carrying the selectable marker gene (Kuroda and Maliga 2001b; Kuroda and Maliga 2001a). Removal of selectable marker genes by loop-out via directly repeated sequences has been shown (Iamtham and Day 2000). However, this is a complicated system that is difficult to control. We have utilized the CRE/lox site-specific recombination system for efficient elimination of the selectable marker genes (Corneille et al. 2001; Hajdukiewicz et al. 2001).

2) Competence of plastids to integrate foreign DNA. The number of plastid genome copies in the leaves of different species is comparable. However, plastid transformation efficiencies are species dependent. Plastid transformation efficiency in bombarded potato and Arabidopsis leaf cultures was 10-fold and 100-fold lower than in tobacco, respectively (Sikdar et al. 1998; Sidorov et al. 1999). Since the chloroplast size and genome copy number, at least in potato, is about the same as in tobacco, we assume, that the difference in the transformation efficiency is due to differences in the efficiency with which foreign DNA is incorporated into the plastid genome.

It is not known how to activate the recombination system of plastids to enhance transformation competence. In accordance with the present invention, methods and compositions employing the phiC31 integrase are provided which enhance the efficiency of plastid transformation in a wider range of plant species.

Site-specific Phage Recombinases for Excision and Integration of Foreign DNA Methods employing two different bacteriophage recombinases for the excision and integration of foreign DNA into the plastid genome of higher plants are described herein. Several prokaryotic and lower eukaryotic site-specific recombination systems have been shown to operate successfully in higher eukaryotes. In yeast, plant and animal cells functional site-specific recombination systems have been described from bacteriophages P1 (CRE-loxP) (see below) and Mu (Gingix), and from the inversion plasmids of *Saccharomyces cerevisiae* (FLP-frt) (Morris et al. 1991; Lyznik et al. 1996) and *Zygosaccharomyces rouxii* (R-RS) (Onouchi et al. 1991; Onouchi et al. 1995). In each of these systems, no additional factor aside from the recombinase and target sequences is required for recombination.

The CRE-loxP site-specific recombination system of bacteriophage P1 has been studied extensively in vitro and in *E. coli* (Craig 1988; Adams et al. 1992; Guo et al. 1997). Expression of the CRE protein (38.5 kDa) is sufficient to cause recombination between 34 bp loxP sites that consist of 13 bp inverted repeats separated by 8 bp asymmetric spacer sequence. If there are two loxP sites within a DNA segment, the result of the recombination reaction depends on the relative position of the recombination sites. If the recombination sites form a direct repeat, that is they are in the same orientation, recombination results in deletion of the intervening DNA. If the recombination sites are in an inverted orientation, CRE-mediated recombination results in an inversion of the intervening DNA. In site-specific DNA integration, recombination between a site on a circular molecule and a site on the chromosome results in the insertion of the circular molecule into the chromosome. However, after integration, the DNA is flanked by two lox sites in the same orientation and therefore can be excised if the recombinase is present. There are many applications for the site-specific recombination systems to study gene function and development. The CRE-loxP system has been explored in higher plants to facilitate intra- and inter-molecular site-specific recombination, removal of selectable marker genes and for site-specific insertion of foreign DNA in the nucleus (Dale and Ow 1990; Odell et al. 1990; van Haaren and Ow 1993; Gleave et al. 1999; Choi et al. 2000; Day et al. 2000). Application of the CRE-lox site-specific recombination system for the removal of marker genes has been reviewed recently (Ow 2001). The CRE-lox site-specific recombination system has been also employed for the removal of selectable marker genes from the plastid genome(Corneille et al. 2001; Hajdukiewicz et al. 2001).

The CRE-lox system is reversible, mediating both excision and integration of sequences flanked by lox sites, with ~100-fold bias in favor of excision. Thus, a better choice for integration is the phage phiC31 integrase (INT) which catalyses integration between non-identical attB and attP sequences (bacterial and phage attachment regions, respectively), and cannot mediate excision without additional factors (Thorpe and Smith 1998). The *Streptomyces* phiC31 integrase catalyses unidirectional integration in its host (Thorpe et al. 2000), and has been successfully utilized for efficient, unidirectional integration of foreign DNA in mammalian cells (Groth et al. 2000; Thyagarajan 2001) and yeast (Thomason et al. 2001). There are three elements of the system: (1) a target site in the genome (attB); (2) a vector with an attP site and (3) integrase (INT) enzyme. The location of the attB and attP are interchangeable: if attP is located in the genome, attB is present in the vector. Minimal sequences required for attB and attP function in vitro were defined to be 34 bp and 39 bp, respectively (Groth et al. 2000). The three bp core, TTG, within which recombination takes place, is shared by attB and attP. There is little sequence similarity outside the core: including the core, only 15 nucleotides are conserved between the minimal attB (34 bp) and attP (39 bp) sequences. The consequence of the lack of sequence similarity between attB and attP is that the recombination products, attL (left junction) and attR (right junction)are very different from the parental sites, and therefore are not recognized by the integrase. In mammalian cells, longer sequences were found to be more efficient (Groth et al. 2000). We describe here the use of phiC31 site-specific recombinase for the insertion of foreign DNA into the plastid genome. Full size 55-bp attB and 217-bp attP regions were utilized in the following experiments.

Alternative Methods for Introducing INT Activity in Higher Plants to Facilitate Transgene Integration The source of INT can be a DNA or RNA template, or purified INT protein may be provided directly. DNA templates encoding INT, may be provided transiently, without stable integration into the plastid or nuclear genomes. In an alternative approach the INT encoding sequence may be expressed in a stable fashion by incorporating the integrase gene into one of the plant's genomes. mRNA sequences encoding INT or the purified INT protein provide a transient, rather than a stable source of INT as both are degraded in the cell over time.

Using a DNA template as the source of INT is compatible with both transient and stable expression of the enzyme. Transient supply of INT in plastids could be ensured by incorporating an INT coding region in a cassette with plastid signals in a Bluescript (or similar bacterial) plasmid. The Bluescript plasmid replicates in *E. coli*, but not in plastids, resulting in rapid elimination of the int gene. If higher levels of INT are needed, and presence of INT over a longer period of time is desirable, the int gene can be incorporated in a shuttle plasmid which is episomally maintained. Shuttle plasmids, such as the NICE plasmid (Staub and Maliga 1994a), are maintained in the absence of any selection for a period of time, but are unstable and eventually lost. To limit the expression of INT to plastids, the N-terminus could be translationally fused with a DNA segment encoding an edited C nucleotide. An exemplary DNA fragment for this purpose is the 22 nucleotide psbL editing segment (Chaudhuri and Maliga 1996) from which translation depends on creating an AUG initiation codon from the ACG codon by RNA editing which is specific to plastids. INT may be transiently expressed from a nuclear gene that is not integrated into the nuclear genome, which encodes an N-terminal extension to target the protein to plastids. Vectors based on plant viruses can also be beneficially employed for transient expression of INT, for example tobacco mosaic virus (TMV) (Kumagai et al. 1995; Kumagai et al. 2000), potato virus X (Rommens et al. 1995), tobacco rattle virus (Ratcliff et al. 2001), gemini viruses (Kanevski et al. 1992; Peele et al. 2001) or by an *Agrobacterium* transient gene expression system (Grimsley et al. 1989).

Alternatively, INT activity is provided from a stably integrated gene. The gene may be expressed in the plastid genome from plastid expression signals with or without an RNA editing segment. Alternatively, INT may be expressed from a nuclear gene, and provided with an N-terminal extension to target INT from the cytoplasm to plastids. The nuclear INT may also be expressed from a regulated promoter (Aoyama and Chua 1997; Martinez et al. 1999; Zuo and Chua 2000; Zuo et al. 2000).

As mentioned above, transient integrase activity in plastids may also be accomplished by introducing mRNA rather than DNA as template to produce the integrase enzyme. Using mRNA as the source of integrase has the advantage of supplying enzymatically active integrase for a brief period, but avoids the need to remove the integrase from the plastid or nuclear genomes. A transient supply of INT can also be provided by injecting the purified protein into the plant cell cytoplasm (with plastid-targeting sequence) or microinjected directly into plastids.

Methods for transient gene expression utilizing PEG, electroporation, microinjection, or biolistic transformation have been described (Maliga et al. 1995; Potrykus and Spangenberg 1995; Gelvin and Schilperoort 1997).

The following examples are provided to facilitate the practice of the present invention. They are not intended to limit the invention in any way.

EXAMPLE 1

Transient INT Expression in Plastids for Site-specific Integration of Foreign DNA There are three components of the transient INT system: 1) a transplastomic recipient line carrying an attB sequence 2) an INT encoding vector for transient expression in plastids and 3) a donor vector for integration which contains an attP sequence, a marker gene and a gene of interest (goi).

The following materials and methods are provided to facilitate the practice of Example 1.

Plastid Vector for the Introduction of an attB Sequence into the Plastid Genome

Figure 2:
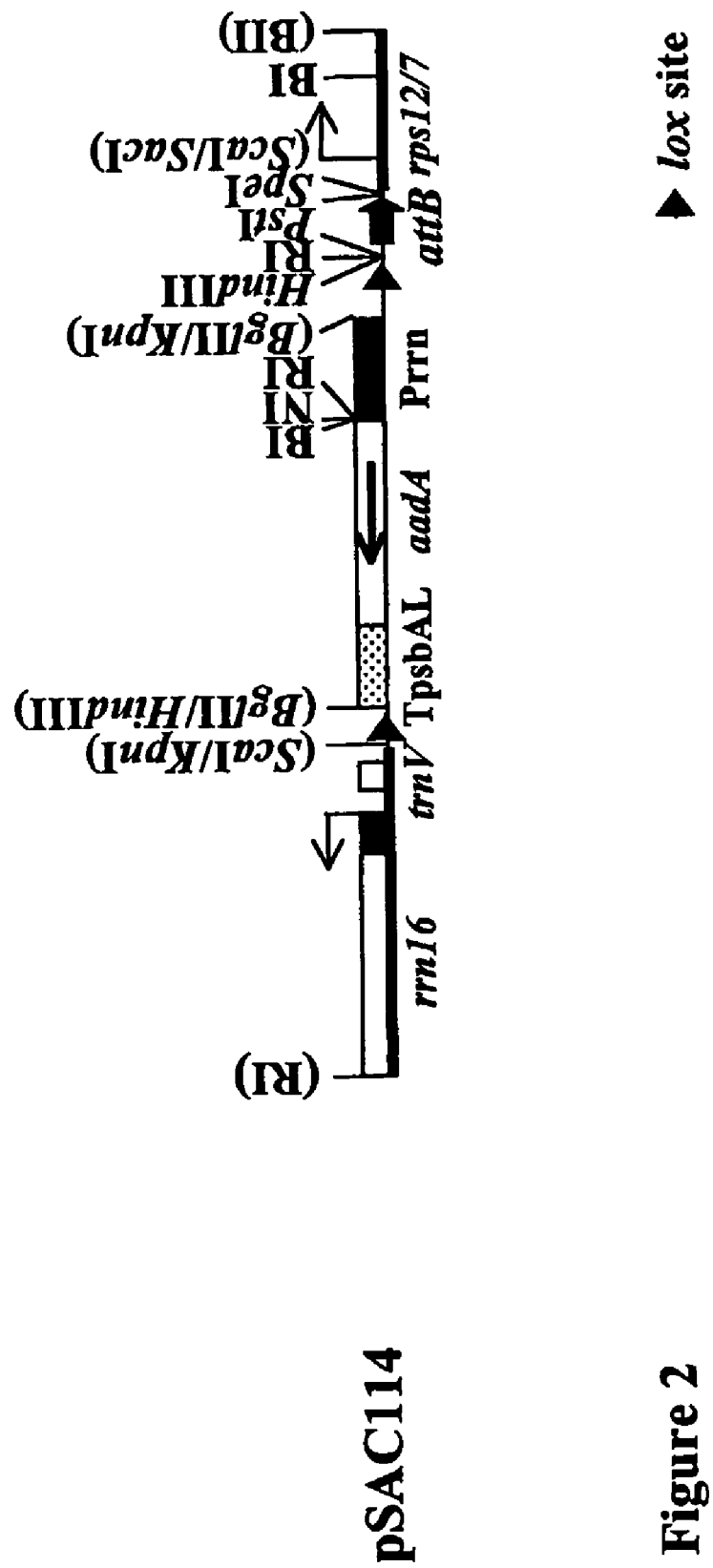
FIG. 2 is a map of plastid transformation vector pSAC114. The vector backbone is pPRV1 (Zoubenko et al. 1994). The (ScaI/KpnI) to (ScaI/SacI) fragment is Seq. ID No. 4. Positions of the plastid genes rrn16, trnV, rps12/7, the aadA gene (flanked by direct lox sites), the attB sequence (Seq. ID No. 3) and the relevant restriction sites are marked.

A plastid transformation vector has been designed that contains an attB sequence and an addA gene that is flanked by two directly oriented lox sites (pSAC114; FIG. 2). The KpnI-SacI region of pSAC114 (Seq. ID. No.4) was assembled in plasmid pSAC113, a pBluescript derivative. Starting from the left, the lox site located downstream of the Tpsba(L) terminator is contained in a KpnI-BglII fragment (SEQ ID NO:2). The fragment was obtained by annealing the complementary oligonucleotides: loxdel1T (SEQ ID NO: 10)5'-GGTAC-CATAACTTCGTATAATGTATGCTATAC-GAAGTTATAGATCT-3' and loxdel1L (SEQ ID NO: 11)5'-AGATCTATAACTTCGTATAGCA TACATTATACGAAGTTATGGTACC-3'. The aadA gene derives from plasmid pZS176 (Prrn:RBS:aadA:TpsbA(L) (Svab and Maliga 1993) and it is contained in a HindIII-KpnI fragment. The lox site located upstream of aadA is contained in a BglII-HindIII fragment (SEQ ID NO: 1) and was obtained by annealing the complementary oligonucleotides: loxdel2T (SEQ ID NO: 12)5'-AGATCTATAACTTCG-TATAATGTATGCTATACGAAGTTATAAGCTT-3' and loxdel2L (SEQ ID NO: 13)5'-AAGCTTATAACTTCGTATA GCATACATTATACGAAGTTATAGATCT-3'. The attB sequence was created from a PstI-SpeI oligonucleotide (SEQ ID NO: 3) by annealing the complementary oligonucleotides: attBPstI (SEQ ID NO: 14)5'-CTGCAGCCGCGGT-GCGGGTGCCAGGGCGTGCCCTTGGGCTC CCCGGGCGCGTACTCCACTAGT-3' and attBSpeI (SEQ ID NO: 15)5'-ACTAGTGGAGTACGCGCCCGGGGAGC-CCAAGGGCACGCCCTGGCACCCGCACCGCGG CTG-CAG-3'. The KpnI-SacI fragment from pSAC113 (SEQ ID NO: 4) was cloned into the ScaI site of pPRV1 (Zoubenko et al. 1994) which contains the rrn16 targeting region to create pSAC114 (FIG. 2).

Integrase Plasmids for Transient Expression of int Gene in Plastids

Figure 3:
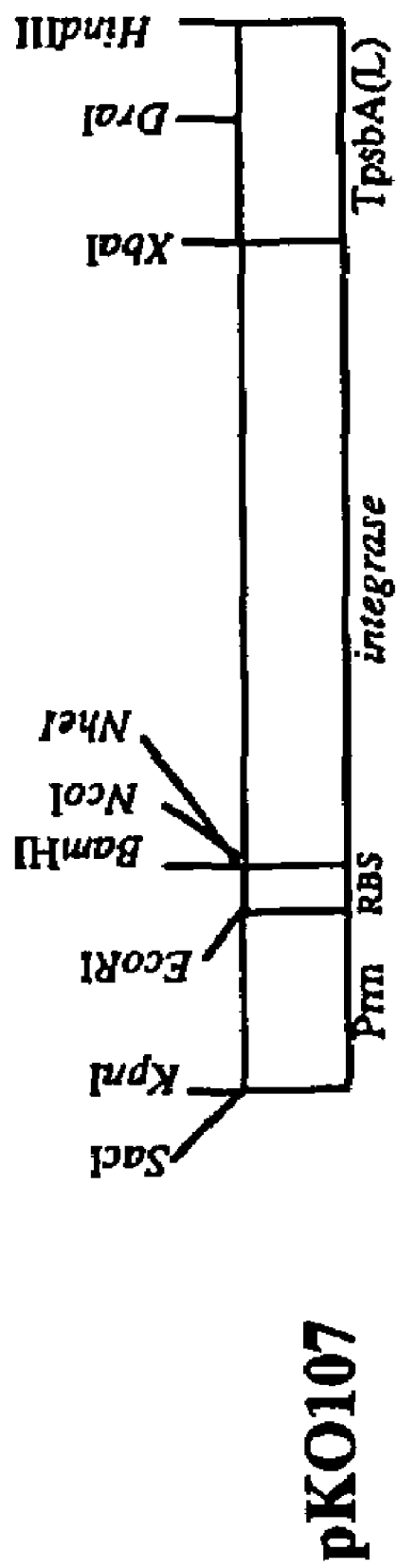
FIG. 3 is the map of the int gene in transient expression plasmid pKO107. SacI-HindIII fragment is Seq. ID No. 25. The int coding region and positions of the relevant restriction sites are marked.

The int gene and attP region of *Streptomyces* phage phiC31 is contained in pSET152 (Wilkinson 2002). To clone the attP sequence and int gene the BglI fragment from pSET152 was introduced into pBS KS+ at the blunted SpeI site to create plasmid pKO81. To express the int from plastid expression signals, the integrase coding region (SEQ ID NO: 5), contained in a BamHI-XbaI fragment, was introduced into pZS176 to replace the aadA coding region and create plasmid pKO107 (SEQ ID NO: 5; FIG. 3). pKO107 does not contain DNA sequences to maintain the plasmid as an episomal element.

Figure 4:
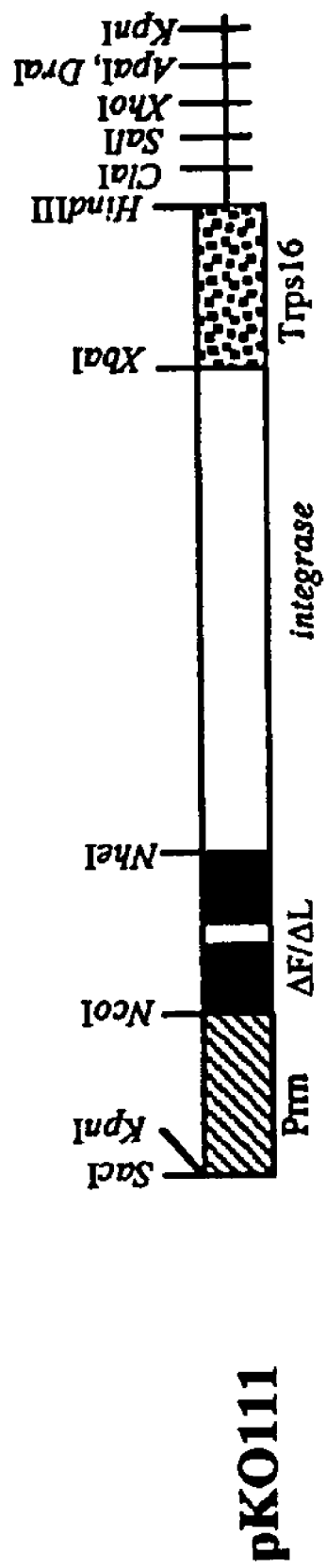
FIG. 4 is the map of the int gene in transient expression vector pKO111. The SacI to HindIII fragment is Seq. ID No. 26. The integrase gene, the deltaF/deltaL psbL editing fragment (Chaudhuri and Maliga 1996) and positions of the relevant restriction sites are marked.
Figure 5:
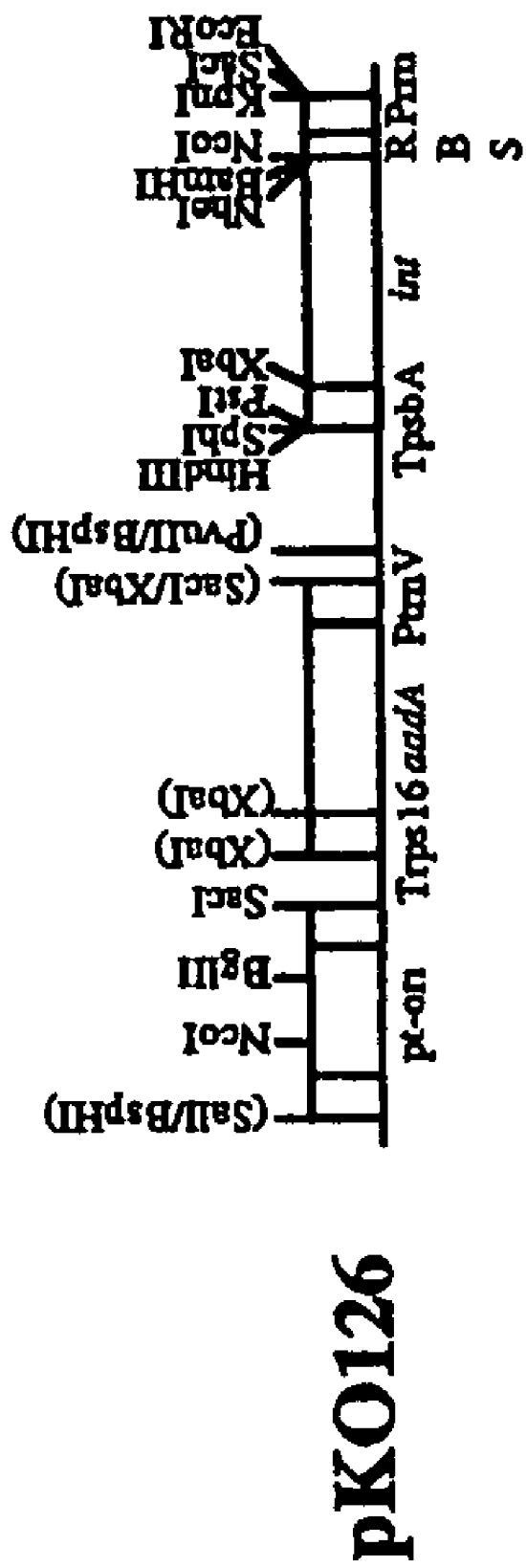
FIG. 5 is a map of the episomally maintained transient int expression vector pKO126. The plastid ori (pt-ori) sequence (Staub and Maliga 1994a), aadA gene, int gene (coding region is Seq. ID No. 5) and the relevant restriction sites are marked.

To restrict integrase expression to plastids an editing dependant int gene was created. pKO111was created by replacing the neo coding region from pSC4 (Chaudhuri and Maliga 1996) with the int coding region, contained in a NheI-XbaI fragment (SEQ ID NO: 5; FIG. 4). pKO111 has the ColE1 replication origin and therefore is not maintained as an episomal element in plastids. In contrast, plasmid pKO126 has both the ColE1 replication origin and the NICE1 sequences that allow episomal maintenance in plastids (Staub and Maliga 1995). Plasmid pKO126 was obtained by replacing the neo coding region with the integrase coding region, contained in an NcoI-XbaI fragment, in a modified version of plasmid pNICER1 (pJS146) (Staub and Maliga 1995) (XbaI blunt; SEQ ID NO: 5; FIG. 5).

Figure 6:
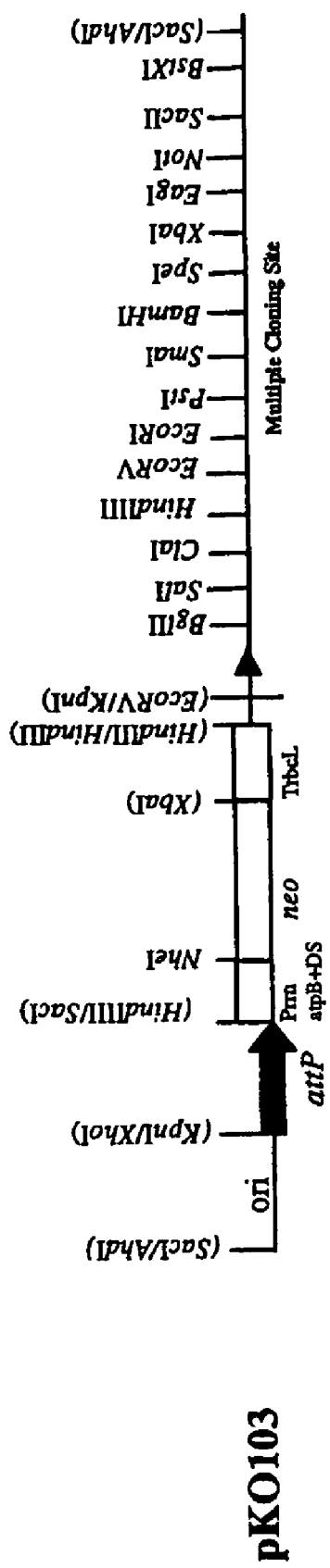
FIG. 6 is a linearized map of donor vector pKO103 (Seq. ID No. 7). A circular representation is shown in FIG. 9A. The attP sequence (Seq. ID No. 6), neo gene, lox site (Seq. ID No. 2) and relevant restriction sites are marked.

Donor Vectors to Provide the neo Gene and attP Sequence for INT Catalyzed Integration The donor vector provides the attP sequence and marker gene sequence (neo), necessary for integrase mediated integration into the plastid genome, as well as a gene of interest. The attP sequence was PCR amplified from pSET152 with primers: attPXhoI (SEQ ID NO: 16) 5'-CAACTCGAG-CAATCGCCCTGGGTG-3' and attPHindIII (SEQ ID NO: 17)5'-CAAAAGCTTCCCGGTCACAACCCCTTG-3' and confirmed by sequencing (SEQ ID NO: 6). pKO102 is a donor vector that contains an attP sequence, a neo marker gene, a lox site and a MCS. The neo gene from pHK10 (Kuroda and Maliga 2001b) was contained in a SacI/HindIII blunt fragment and has been modified by blunting the XbaI site at the 3' end of the coding region. The lox site is contained in a KpnI-BglII fragment (SEQ ID NO: 2). To remove the ampicillin resistance gene and the f1 replication origin, plasmid pKO102 was digested with the AhdI-SacI enzymes, blunted and ligated to create plasmid pKO103 (SEQ ID NO: 7; FIG. 6). A gene of interest can be added to the donor vector at the multiple cloning site sequence (MCS).

Recipient Transplastomic Tobacco Plants with an attB Sequence and a lox Site

Figure 7C:
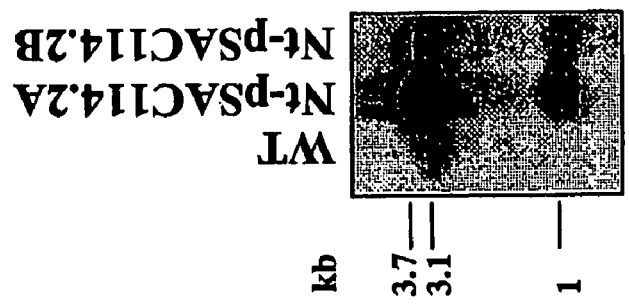
FIG. 7 shows maps of (A) the wt and (B) pSAC114 transformed plastid genomes and (C) a DNA gel blot to confirm plastid DNA structure. Total cellular DNA was digested with the BamHI restriction endonuclease and probed with the wild-type EcoRI-EcoRV plastid DNA fragment (heavy line). The size of hybridizing fragments is marked in the wt and Nt-pSAC114 maps. The Nt-pSAC114.2A DNA sample is homoplasmic for the transformed plastid genome structure, while Nt-pSAC114.2B still has some wt plastid genome copies present. Positions of the plastid genes rrn16, trnV, rps12/7, the aadA gene (flanked by direct lox sites), the attB sequence and the relevant restriction sites are marked.
Figure 7A:
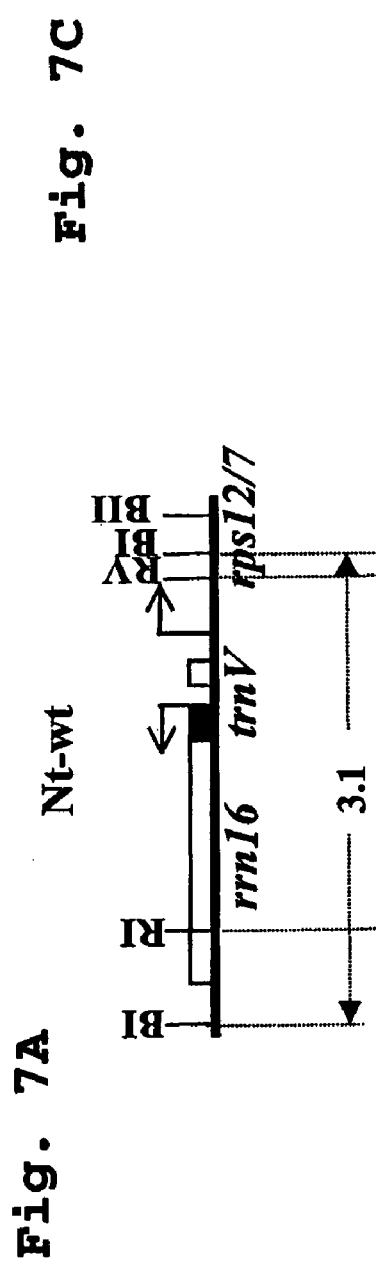
Figure 7B:
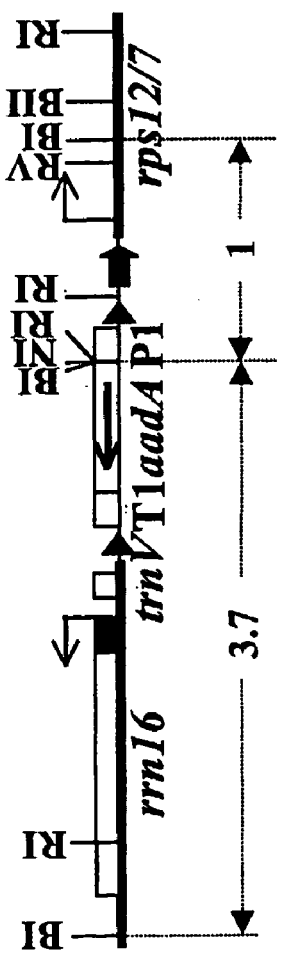
Figure 8:
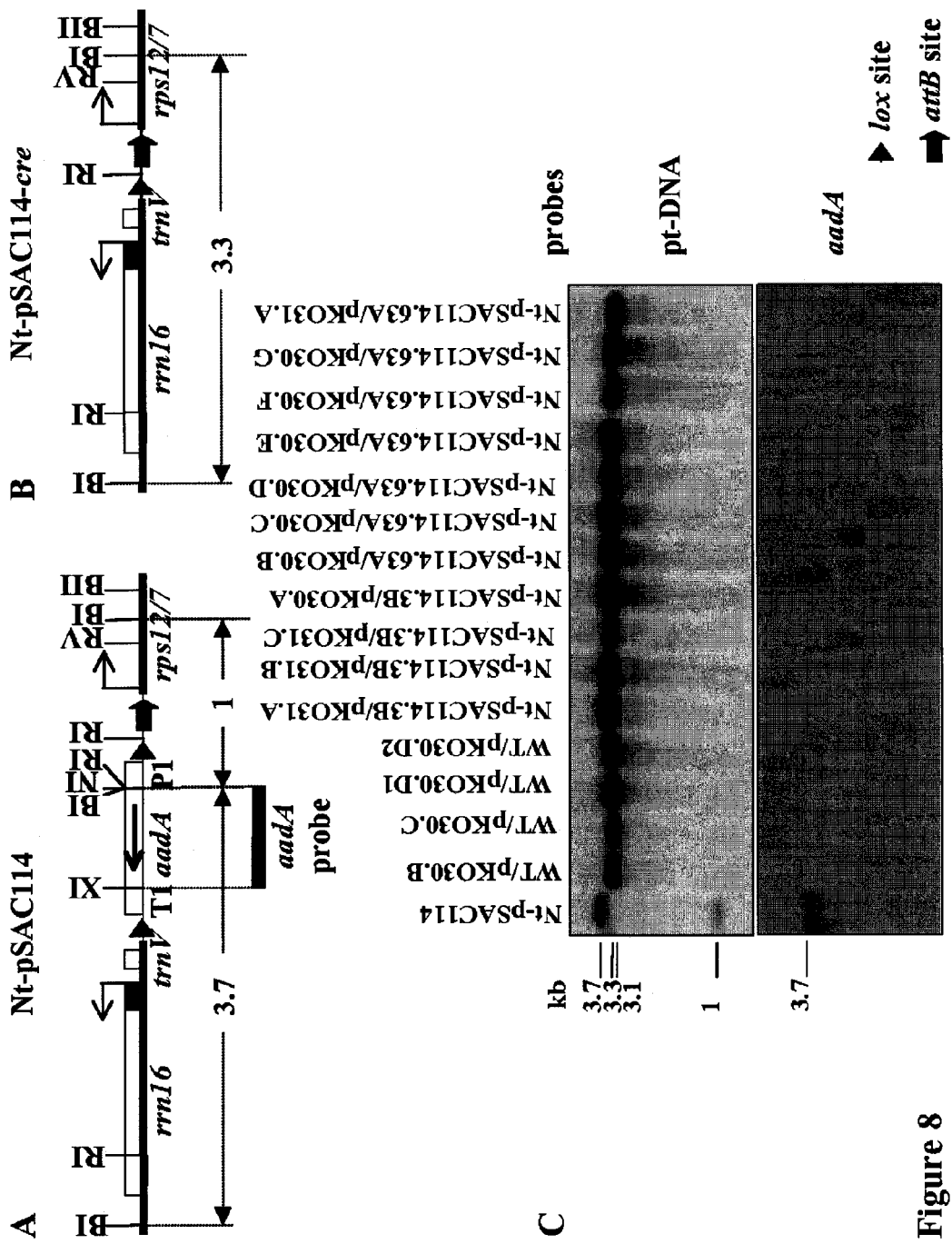
FIG. 8 shows (A) a partial map of the Nt-pSAC114 plastid genome (B), Nt-pSAC114 plastid genome after excision of aadA by CRE, (C) a DNA gel blot to confirm plastid DNA structure after aadA excision. Excision of aadA in the Nt-pSAC114 plastid genome was triggered by transformation with *Agrobacterium* carrying cre plasmids pKO30 (TP22) or pKO31 (TP5). Total cellular DNA was digested with the BamHI restriction endonuclease and probed with plastid DNA (EcoRI-EcoRV) and aadA (NcoI-XbaI) fragments. Fragments hybridizing with the ptDNA probe are marked in FIG. 7; those with aadA in this Fig. Note absence of aadA in CRE-transformed plants. Position of plastid genes rrn16, trnV, rps12/7, the aadA gene, lox sites, attB sequence and the relevant restriction sites are marked.

Plastid transformation vector pSAC114 carries an attB sequence and an aadA gene flanked by two lox sites in direct orientation (FIG. 2). Plastid transformation using the biolistic protocol, selection of transplastomic tobacco clones (RMOP medium, 500 mg/L Spectinomycin dihydrochloride) and characterization of the transplastomic clones by DNA gel blot analysis has been described previously (Svab and Maliga 1993). Transformation with pSAC114 yielded a number of independently transformed transplastomic lines, of which 3 were purified to the homoplastomic state: Nt-pSAC114-2A, Nt-pSAC114-3B and Nt-pSAC114-5A. All three lines are considered identical other than that they have been generated independently. A uniform population of transformed plastid genomes in the transplastomic plants was verified by DNA gel blot analysis (FIG. 7). The aadA gene was removed by a plastid-targeted nuclear-encoded cre introduced by *Agrobacterium* transformation or pollination (Corneille et al. 2001; Hajdukiewicz et al. 2001). The plastid genome of the resulting plants contains only one lox site and an attB sequence (FIG. 8).

INT-mediated Integration of a neo Donor Vector into the Nt-pSAC114 attB Sequence To test for integrase-mediated insertion of the neo gene, a donor vector (pKO103) and an int encoding vector (pKO107, pKO111 or pKO126) were introduced into the plastids of Nt-pSAC114 plants by the biolistic process (FIG. 9). Clones with an integrated donor vector were selected on kanamycin containing (25 mg/L or 50 mg/L) RMOP medium. Examples for clones which were obtained by integrase-mediated neo gene insertion are Nt-pSAC114-2B/pKO111, Nt-pSAC114-2A-5/pKO107 and Nt-pSAC114-3B-1/pKO107. Clone Nt-pSAC114-2B/pKO111 was obtained by INT-mediated integration expressed from pKO111, a plasmid carrying an editing dependent int (E-int), and ColE1 ori. Donor integration in the clones Nt-pSAC114-2A-5/pKO107 and Nt-pSAC114-3B-1/pKO107 was mediated by int expressed from plasmid pKO107 (no editing signals; ColE1 ori only).

Figure 11:
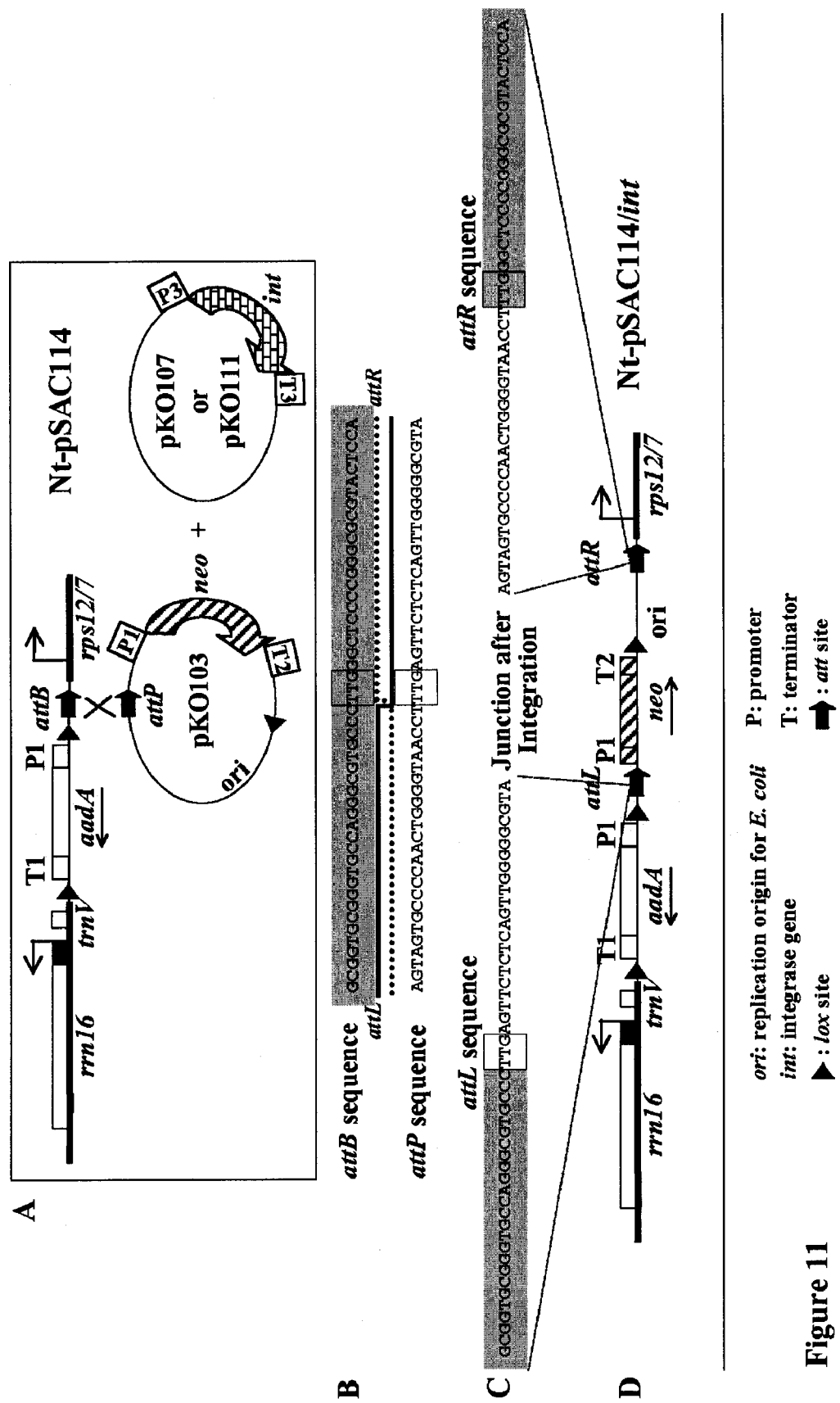
FIG. 11 shows (A) the components for INT-mediated integration of the pK0103 donor vector into the Nt-pSAC114 plastid genome. Transient INT function is provided by plasmids pK0170 or pKO111. (B) The aligned attB and attP sequences. The attB sequence corresponds to nucleotides 9-58 of SEQ ID NO: 3 and the attP sequence corresponds to nucleotides 137-186 of SEQ ID NO: 6. (C) The attL and attR sequences formed by INT-mediated recombination of attB and attP sequences. The attL sequence corresponds to nucleotides 5-54 of SEQ ID NO: 8 and the attR sequence corresponds to nucleotides 134-183 of SEQ ID NO: 9. (D) The product of INT-mediated integration of the pK0103 donor vector in the Nt-pSAC114 plastid genome. Plastid genes rrn16, trnV, rps12/7, the aadA gene (flanked by direct lox sites), the attB sequence, the attR sequence, the neo gene, the attL sequence, an attR sequence, a third lox site and the relevant restriction sites are marked.

Insertion of neo into the plastid genome was tested by PCR amplification (FIG. 10). Two separate PCR reactions were performed using 1) primers 136 (SEQ ID NO: 18) (aadA; 5'-CCGCCAGCGTTCATCCTGAGC-3') and neoAL (SEQ ID NO: 19) (5'-TGACAGCCGGAACACGGCGGC-3') or 2) primers neoAU (SEQ ID NO: 20) (5'-TGAAGAGCTTG-GCGGCGAAT-3') and 191 (SEQ ID NO: 21) (5'-GAGATG-TAACTCCAGTTCC-3'). For PCR reaction 1 a 1 kb fragment was expected if neo integrated by attB-attP recombination. For PCR reaction 2 a 2 kb fragment was expected if integration of the neo gene occurred. Perfect reconstituted attL (SEQ ID NO: 8) and attR (SEQ ID NO: 9) sequences were confirmed in Nt-pSAC114-2B/pKO111 by direct sequencing of the amplification products (FIG. 11). Integration events were also confirmed in positive clones Nt-pSAC114-2A-5/pKO107 and Nt-pSAC114-3B-1/pKO107 by direct sequencing of PCR products. The primers used for sequencing the junctions were 191 (SEQ ID NO: 21), attPHindIII (SEQ ID NO: 17) and attPXhoI (SEQ ID NO: 16).

Figure 12A:
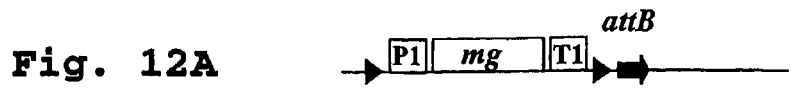
FIG. 12 is a schematic design for integration of foreign DNA mediated by transient expression of INT in plastids. Shown are (A) the plastid genome containing a marker gene (mg) flanked by two directly oriented lox sites (Seq. ID No. 1) and an attB site (Seq. ID No. 3). (B) The recipient plastid genome containing one lox site and an attB site after CRE mediated deletion of the marker gene. (C) The donor vector carrying an attP site (Seq. ID No. 6), ColE1 ori, a marker gene (mg), one lox site and a gene of interest (goi) and the int plasmid for transient expression of INT. (D) The plastid genome after INT mediated insertion of the donor vector. attL and attR sequences (Seq. ID No. 8 and Seq. ID No. 9 respectively) were generated by INT mediated attB-attP recombination. (E) The plastid genome after CRE mediated excision of attL and the marker gene.
Figure 12B:

A transplastomic recipient line may be created by introducing the attB sequence into the plastid genome using spectinomycin resistance (aadA gene) as a selective marker. The aadA gene is flanked by directly oriented lox sites, so that it can be removed by CRE. An example for a vector suitable to obtain the progenitor of an attB recipient is plasmid pSAC114 (FIG. 2) (KpnI-SacI fragment; SEQ ID NO:4). The aadA gene may be removed by a nuclear-encoded CRE (Corneille et al. 2001), the product of which is shown in FIG. 12B. Tobacco plant lines with an attB site and a lox site (no aadA) are Nt-pSAC114-pKO30 and Nt-pSAC114-pKO31 (FIG. 8C).

Transient expression of the int gene may be obtained from multiple, alternative vectors. These vectors differ with respect to sequences that sustain replication: some have only sequences for replication in *E. coli* (ColE1 ori) but not in plastids (pKO107, FIG. 3; pKO111, FIG. 4), others have the ColE1 replication origin and plastid sequences that sustain episomal maintenance (Staub and Maliga 1994a) (pKO126, FIG. 5). The INT in plasmid pKO111 at its N-terminus is translationally fused with the psbL editing segment (Chaudhuri and Maliga 1996), so that translation of the Eint (edited INT) mRNA is dependent on conversion of an ACG codon into an AUG translation initiation codon by RNA editing. Editing-dependent int is not expressed in *E. coli* (prokaryotes) or in the plant's nucleus (Hoch et al. 1991; Maier et al. 1996; Bock et al. 1997; Chaudhuri and Maliga 1997). Expression of int in plasmids pKO107 and pKO126 is from (non-edited) plastid signals. The schematic design of transient INT vectors is shown in FIG. 12C.

Figure 12C:
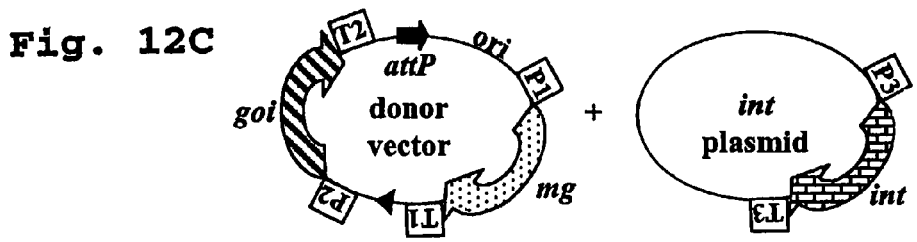
Figure 12D:
Figure 12E:

Donor vectors contain an attP sequence, a marker gene, a lox site and a gene of interest (goi) (FIG. 12C). The donor vector will be provided at the same time as the int plasmid. INT mediated recombination between the attB and attP sequences will result in integration of the donor vector into the recipient plastid genome, as shown in FIG. 12D. After recombination, the plastid genome contains a lox site, an attL sequence, a marker gene, a second lox site, a goi and an attR sequence. The marker gene (all sequences between the lox sites) can be subsequently removed by a plastid-targeted CRE. The resulting plants contain one lox site, a goi and an attR sequence (FIG. 12E). The cre gene, and the linked marker gene, can then be crossed out in the seed progeny to obtain cre- and marker-free plants containing a goi in the plastid genome.

The general scheme for transient INT-mediated insertion of the Donor vector is depicted in FIG. 12. The marker gene or genes used for the introduction of attB is not limited to aadA, and the marker gene or genes carried by the Donor vector are not limited to the neo gene, but could be any gene that confers a selectable or screenable phenotype to the plant cell suitable to achieve plastid transformation.

Figure 9A:
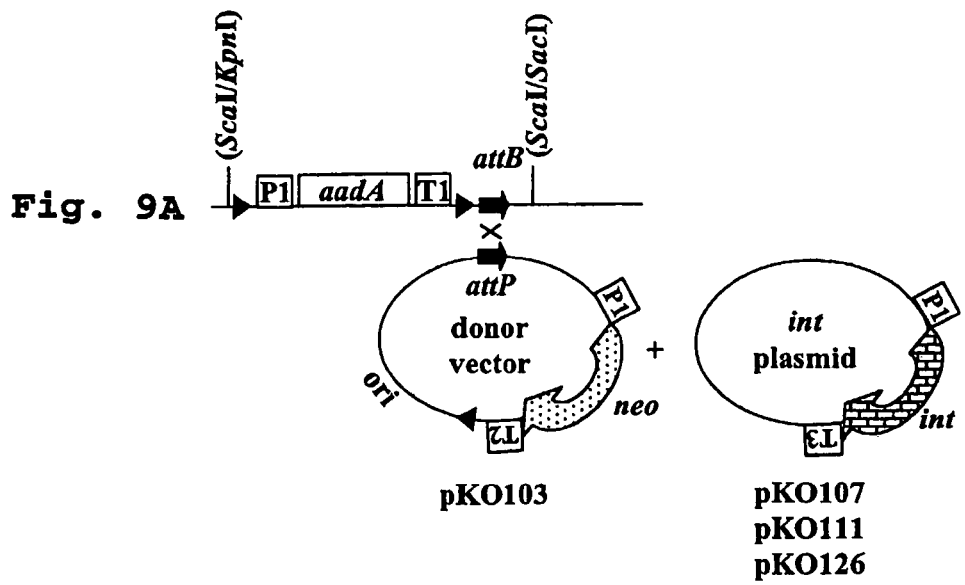
FIG. 9 is the schematic experimental design for integration of the neo gene mediated by transient expression of INT in plastids. Shown are (A) The transformed plastid genome containing the aadA gene flanked by two directly oriented lox sites and an attB site (the KpnI-SacI sequence derives from pSAC113, Seq. ID No.4); the donor vector pKO103, carrying an attP site, a neo gene and one lox site (Seq. ID No. 7), and a plasmid for transient expression of INT (coding region Seq. ID No.5) (pKO107, pKO111, or pKO126). (B) The plastid genome obtained after INT mediated insertion of the neo gene and a lox site. attL and attR sequences were generated by INT mediated attB-attP recombination.
Figure 9B:
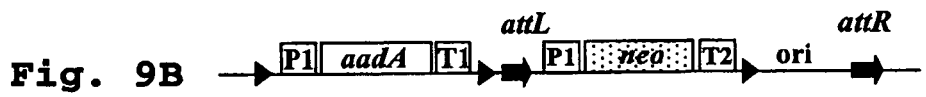

A working example, in which the aadA marker gene has not been removed from the recipient plastid genome, is shown in FIG. 9A. The INT was transiently expressed from plasmids pKO107 and pKO111. The donor vector pKO103 contains an attP sequence, a neo gene as a selectable marker, a lox site, and no gene of interest (FIG. 9A). The product of stable integration of the neo gene in the plastid genome via attB and attP recombination is shown in FIG. 9B, and is described in Example 1. The plastid genome of resulting plants contain: an aadA gene flanked by two lox sites; an attL sequence; a neo gene; a third lox site in direct orientation with the other two lox sites; the ColE1 ori of the Bluescript plasmid, that is the backbone of the donor vector; and an attR sequence (FIG. 9B).

EXAMPLE 2

Site-specific Integration of Foreign DNA by a Plastid Encoded Integrase

In Example 2, we describe a method for integration of the donor vector by INT expressed from a gene stably integrated in the plastid genome. Stable plastid expression of int may yield higher levels of INT resulting in an increase in integration efficiency as compared to transiently expressed INT, which was described in Example 1. Example 2 describes two systems for stable expression of the plastid int gene yielding the same result, a gene of interest, one lox site and attR sequence incorporated in the plastid genome. The two systems differ with respect to the number of marker genes required (System 2A requires one, whereas 2B requires two marker genes) and flexibility to choose the promoter for the expression of gene of interest (2A, no flexibility; 2B, flexible).

Figure 13A:
FIG. 13 is a schematic design of System 2A for integration of foreign DNA mediated by a plastid encoded INT. Shown are (A) the plastid genome containing a promoter (P1), RBS, an aadA coding region flanked by two directly oriented lox sites, RBS, an int coding region, a terminator (T1) and an attB site. This plasmid is the progenitor of recipient plastid site. (B) The recipient plastid genome after CRE excision. It contains only P1, one lox site, a RBS and an int coding region, a terminator (T1) and an attB site.(C) The donor vector carrying an attP site, a marker gene (mg), ColiE1 ori, one lox site, a RBS, coding region of the gene of interest (goi) and terminator (T3). (D) The plastid genome after INT mediated insertion of the donor vector. attL and attR were generated by INT mediated attB-attP recombination. (E) The plastid genome after CRE mediated deletion of the int gene, attL and the marker (mg) gene.
Figure 13B:

System 2A calls for a recipient with a plastid-encoded integrase flanked by a lox site and an attB sequence (FIG. 13B). The recipient may be created by transformation with the plastid vector shown in FIG. 13A. The aadA-int dicistronic operon shown in FIG. 13A is expressed in a cassette with P1 and T1, a plastid promoter and terminator. In this construct the aadA coding region is flanked by two lox sites in direct orientation and the pt-int coding region is cloned next to it. An attB sequence is cloned downstream of the T1 terminator to facilitate INT-mediated integration of the donor vector. The desired recipient is obtained by CRE-mediated excision of the aadA coding region (FIG. 13B). The int gene is now located directly downstream of P1 from which it is expressed. Segregating out the nuclear cre gene in the seed progeny completes construction of the recipient for System 2A.

Figure 13C:
Figure 13D:
Figure 13E:

The donor vector for System 2A carries the attP sequence, a plastid-selectable marker gene (mg), a lox site and a goi (FIG. 13C. This donor vector is a derivative of pKO103 (FIG. 6; SEQ ID NO:7) which lacks a goi. The marker gene has its own expression signals (P2, T2); the goi has only a RBS and T3 sequence. INT-mediated integration events are selected by the expression of the marker gene carried by the donor vector. This marker gene can be any selectable marker, as the recipient no longer carries a marker gene. Integration results in the insertion of the donor plasmid at the attB site (FIG. 13D). The marker gene and the integrase are subsequently removed by CRE. This will result in expression of the goi from the P1 promoter (FIG. 13E). Cre will then be segregated out from the plants in the seed progeny as a final step to obtain the desired end product. The P1, P2 and T1, T2 and T3 are variants of plastid expression signals. Some examples of promoter and terminator sequences that could be used are: Prrn, PsbA, ptrnV and TpsbA, TrbcL, Trps16 described in (Staub and Maliga 1993; Svab and Maliga 1993; Staub and Maliga 1994b; Zoubenko et al. 1994), U.S. Pat. No. 5,877,402.

System 2B is based on a recipient in which int and aadA are expressed as a dicistronic operon (FIG. 14A). The donor plasmid for System 2B is the same as for System 2A, except that the goi has its own promoter (P3). Clones carrying the integrated donor are selected by expression of the marker gene (for example neo, as shown in FIG. 14). INT-mediated integration yields a complex structure shown in FIG. 14C. The desired end product, a plastid genome containing the goi, is obtained by CRE-mediated excision of int, aadA and the neo genes (FIG. 14D). Segregating out the nuclear cre gene in the seed progeny completes construction of the recipient for System 2B.

EXAMPLE 3

Site-specific Integration of Foreign DNA into the Plastid Genome Facilitated by a Nuclear-encoded Plastid Targeted int The following materials and methods are provided to facilitate the practice of Example 3.

Plastid Targeted N-int Linked to a Nuclear Gentamycin Resistance Gene

Figure 15:
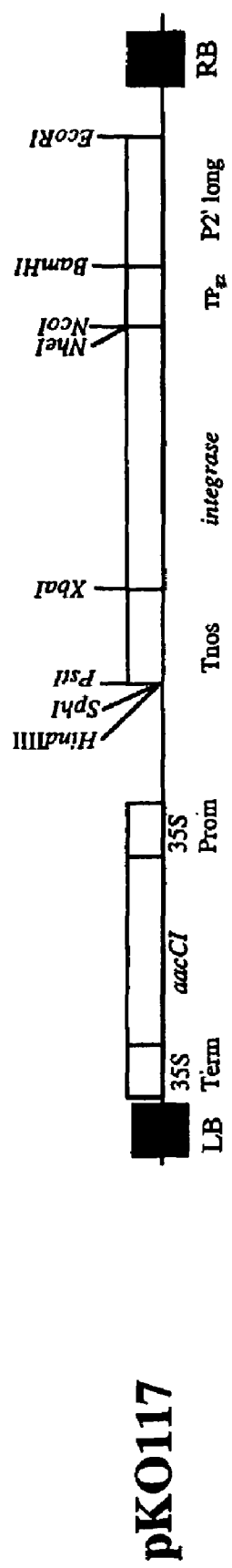
FIG. 15 is a schematic design for integration of foreign DNA mediated by nuclear encoded plastid targeted INT. Shown are (A) the recipient plastid genome containing one lox site and an attB site. INT is expressed from a nuclear gene. (B) The donor vector carrying an attP site, ColE1 ori, a marker gene, one lox site and a gene of interest (goi). (C) Plastid genome obtained after INT mediated insertion of donor vector. attL and attR sequences were generated by INT mediated attB-attP recombination. (D) The plastid genome after CRE mediated excision of attL, the ColE1 ori and the marker gene.

The N-int gene in *Agrobacterium* vector pKO117 encodes INT with its N terminus translationally fused with the pea Rubisco small subunit (SSU) chloroplast transit peptide (Timko et al. 1985) and twenty-two amino acids of the mature Rubisco small subunit. The int coding region is contained in an NcoI-XbaI fragment (SEQ ID NO: 5). Plasmid pKO117 was obtained by replacing the cre coding region with the int coding region in plasmid pKO30 (WO01/21768). The map of *Agrobacterium* transformation vector pKO117 is shown in FIG. 15.

To obtain suitable recipients, transformation of Nt-pSAC114 transplastomic lines (Example 1) was carried out with *Agrobacterium* vector pKO117. Transformation and tobacco plant regeneration was carried out as described (Hajdukiewicz et al. 1994). Briefly, nuclear gene transformants were selected by gentamycin resistance on RMOP shoot regeneration medium containing 100 mg/L gentamycin and 500 mg/L carbenicillin. Gentamycin resistance of the shoots was confirmed by rooting on plant maintenance (RM) medium containing 100 mg/L gentamycin. These plants contain an attB site and a lox site in the plastid genome and express an N-int in the nucleus, are suitable recipients for transformation with suitable donor vectors of the invention.

Figures 16A, 16B:
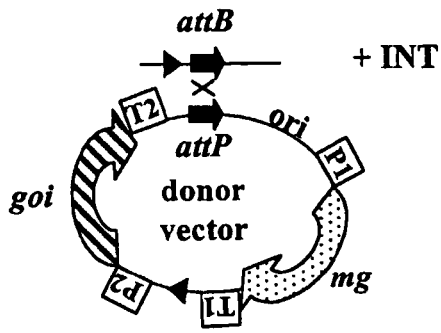
FIG. 16 shows the map of the T-DNA region in *Agrobacterium* binary vector pKO117. The *Agrobacterium* binary vector has the pPZP222 backbone (Hajdukiewicz et al. 1994) and is a pKO30 derivative as described in WO 01/21768. The int gene sequence (EcoRI-PstI) is Seq. ID No. 27. Positions of left and right borders (LB and RB), the gentamycin resistance gene (aacC1), nopaline syntase untranslated 3' end (Tnos), int coding region, transit peptide fragment (TP22), 2' *Agrobacterium* promoter (P2') and the relevant restriction sites are marked.
Figure 16C:
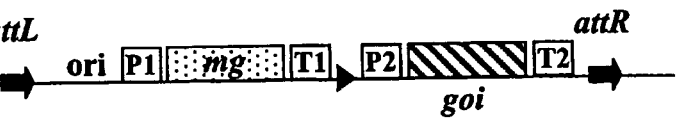
Figure 16D:

The system described in Example 3 relies on a nuclear-encoded, plastid-targeted integrase gene (N-int) for INT activity in plastids. The only difference between the systems described in Example 1 and Example 3 is that in Example 1 INT is provided by a plastid construct transiently expressed in plastids whereas in Example 3 it is provided by a nuclear gene. The transplastomic recipient line carries an attB sequence and a lox site, as shown for Example 1. The donor vector contains an attP sequence, a marker gene, a lox site and a gene of interest (goi) (FIG. 16B). The donor vector is introduced into the plastids by a suitable method (biolistic transformation, PEG treatment, and electroporation), and clones carrying the insertion are selected by the marker gene encoded in the donor vector (FIG. 16C). The marker gene or genes in the donor vector can be any gene that confers a selectable or screenable phenotype to the plant cell suitable to achieve plastid transformation. The marker gene and attL are subsequently removed by a nuclear-encoded plastid-targeted CRE. The resulting plants contain one lox site, a goi and an attR sequence (FIG. 16D). The cre gene, and the linked marker gene, can then be crossed out in the seed progeny to obtain cre-and marker-free plants containing a goi in the plastid genome.

EXAMPLE 4

Introduction of the Bar Gene into the Plastid Genome Using INT

The INT site-specific integrase is a useful enzyme to efficiently incorporate the transforming DNA into the plastid genome. Example 4 describes incorporation of a bar gene into the plastid genome using the integrase system. The bar gene has been shown to confer herbicide resistance to transplastomic plants (Lutz et al. 2001). In this example, incorporation of a bar is exemplified in the plastid genome from a suitable donor vector. INT activity for integration can be provided by any of the methods described in this application, from a transient or stable int expressed in the plastid or nuclear genetic compartments.

Figures 17A, 17B, 17C, 17D:
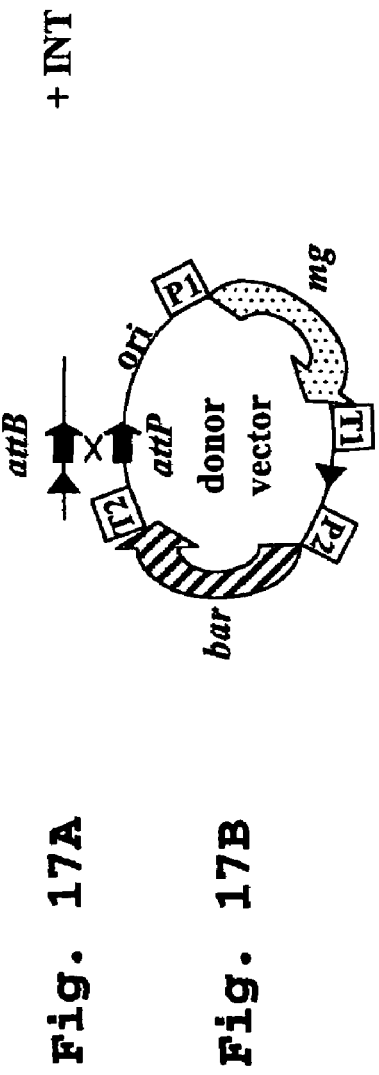
FIG. 17 is a schematic design for INT mediated integration of bar in the plastid genome. Shown are (A) the recipient plastid genome containing a lox site and an attB site. INT is provided transiently from a plastid or nuclear gene. (B) The donor vector carries an attP site, ColE1 ori, a marker gene (P1, T1), one lox site and a bar gene (P2, T2). Suitable bar genes are described in (Lutz et al. 2001). (C) The plastid genome after INT mediated insertion of donor vector. attL and attR sequences were generated by INT mediated attB-attP recombination. (D) The plastid genome after CRE mediated excision of attL and the marker gene.

As described herein, introduction of bar is accomplished using two different recipients. One of the recipients has a lox site and an attB site, i.e., the same recipient that was used in Example 1 and Example 3, shown in FIG. 12B, FIG. 16A and FIG. 17A. The donor vector is shown in FIG. 17B, and is identical with donor vector shown in FIGS. 12C and 16B except, that bar is the gene of interest. Plastid genomes with integrated copies of the bar donor vector can be selected by the expression of the marker gene conferring resistance to spectinomycin, streptomycin, (Svab et al. 1990; Svab and Maliga 1993) kanamycin (Carrer et al. 1993) or resistance to betaine aldehyde (Daniell et al. 2001). After the marker gene and bar gene integrate into the plastid genome by attP-attB mediated recombination (FIG. 17C), the marker gene and the attL site can be removed by a variety of methods. These include introducing the nuclear cre gene into the plants by crossing, direct *Agrobacterium* transformation, transiently expressing CRE from a DNA or RNA template, or introducing the CRE enzyme directly by microinjection. The plastid genome after removal of the marker gene is shown in FIG. 17D. If a stably integrated cre was used, the nuclear cre gene will be removed by segregation in the seed progeny.

The second recipient, in addition to a lox site and attB sequence, has a permanently incorporated plastid promoter P1 transcribing the lox sequence and attB (FIG. 18B). Transcription of the attB sequence may enhance integration efficiency. The marker gene and the bar gene (or other genes of interest) in the bar donor vector are expressed as a dicistronic operon with an RBS and a lox site upstream of bar (FIG. 18C). Integration events are selected by expression of the marker gene, which is subsequently removed by the CRE.

The second recipient is compatible with a variant of the dicistronic donor vector, in which the plastid marker gene has no functional promoter (FIG. 18D). The plastid marker of this donor vector is not expressed in *E. coli*, therefore the ampicillin resistance gene in this vector cannot be removed. Integration of the donor vector at the attB site results in expression of the marker gene and of the bar gene. The marker gene is subsequently removed by CRE (FIG. 18G), resulting in the bar gene expressing from the P1 promoter incorporated in the plastid genome. The nuclear cre gene is removed by segregation in the seed progeny. The advantage of the system is that it requires only one functional plastid promoter.

EXAMPLE 5

Elimination of Marker Genes Using a Negative Selection Scheme for Transient Expression of CRE To decrease the time necessary for the CRE-mediated elimination of marker genes from the plastid genome a negative selection scheme is provided herein. In this Example, we use only transiently expressed CRE recombinase for the removal of DNA sequences. Transiently expressing CRE will eliminate the need to stably integrate cre into the plant genome and remove it after deletion has occurred. Because transiently expressed CRE not expected to eliminate all DNA sequences, a negative selection scheme must be used so that genome copies, which lack a negative selective marker, are preferentially maintained. CRE can be expressed transiently either from a plastid gene encoded in a non-integrating vector or from a non-integrated nuclear gene which is fused to a transit peptide. One example of a negative selection marker gene is the codA gene. codA is bacterial gene encoding cytosine deaminase (CD; EC 3.5.4.1), which is absent in plants. Expression of codA plastids make tobacco cells sensitive to 5-fluorocytosine (5FC) (Serino and Maliga 1997). Thus, 5FC resistance can be used for positive identification of cells with CRE-induced codA deletion, even if the deletion events are relatively rare (Corneille et al. 2001) In one embodiment, the codA is translationally fused with a positive selectable marker. The aadA gene accepts C-terminal fusions, thus aadA C-terminus may be translationally fused with the codA N-terminus by replacing the gfp coding region in plasmid pMSK56 or pMSK57 (Khan and Maliga 1999) from plasmid pGS104 or pGS107 (Serino and Maliga 1997) as NcoI-XbaI fragments. The neo gene does not accept C-terminal fusions, thus the codA C-terminus should be fused with the neo N-terminus. If necessary, protein stability may be improved by including a 16-mer flexible junction peptide between the proteins, such as (SEQ ID NO: 28) ELVEG-KLELVEGLKVA (SEQ ID NO: 22; 5'GAACTTGTTGAA-GAAAATTGGAGCTAGTAGAAGGTCTTAAAGTCGCC-3') reported for the aadA-gfp fusion protein (Khan and Maliga 1999) (WO 00/07421). Depending on the nature of the fusion proteins, shorter (10-mer) and longer flexible junction peptides may be suitable to link CD and the protein that confers the selectable phenotype. A suitable 10-mer peptide would be (SEQ ID NO: 29) ELAVEGKLEA encoded in (SEQ ID NO: 23) 5'-GAACTTGCAGTTGAAGGAAAATTGGAGGCC-3'.

The recipient plastid genome has a lox site and an attB site, and it is the same recipient that was used in Example 1, Example 3 and Example 4, and is shown in FIG. 12B, FIG. 16A, FIG. 17A and FIG. 19A. The donor vector is also shown in FIG. 19B, and is identical with donor vector shown in FIG. 12C except, that the marker gene encodes an AAD-CD fusion protein encoded in an aadA:codA fusion gene. Plastid genomes with integrated donor copies are selected by spectinomycin resistance. When the homoplastomic state is achieved, CRE is transiently expressed in the plastid and initiates aadA:codA excision. The product of excision, a plastid genome with a lox site, a gene of interest and an attR sequence, is shown in FIG. 19D. Clonal lines in which aadA:codA has been excised can be positively identified by 5FC resistance.

EXAMPLE 6

Plastid Transformation and Elimination of Marker Genes Relying on Transiently Expressed Site-specific Recombinases and a Negative Selection Scheme In vegetatively propagated crops, such as fruit trees, strawberries, ornamental plants, forest trees, and potato going through a seed progeny is prohibitive as these plants are highly heterozygous and it would not be possible to recover the original commercial cultivars in the seed progeny. Engineering the plastid genome of these crops may be accomplished by transiently expressed site-specific recombinases as set forth in this example.

Integration of donor sequences will be accomplished by relying on natural attB or attP sites that may be identified empirically by integration of donor vector in plastids with INT activity. Such functional att sites have been identified in the human and mouse nuclear genomes (Thyagarajan 2001). Clones with integrated copies of the donor vector will be identified by the expression of a positive marker gene. The marker genes may confer resistance to spectinomycin, streptomycin, (Svab et al. 1990; Svab and Maliga 1993) kanamycin (Carrer et al. 1993) or resistance to betaine aldehyde (Daniell et al. 2001) (GenBank Accession No. M31480). Plastid transformants may also be selected by utilization of sugars, such as mannose, bu expression of the enzyme phosphomannose isomerase (ManA) (Joersboro et al. 1998; Negrotto et al. 2000) or on xylose by expression of xylose isomerase (XylA) in chloroplasts (Haldrup et al. 1998). The bar gene, conferring PPT resistance (Lutz et al. 2001); aacC1 gene, conferring gentamycin resistance (Carrer et al. 1990) and hph (hygromycin phosphotransferase) conferring hygromycin resistance (SEQ ID NO: 24) (Gritz and Davies 1983) (GenBank Accession No. K01193) are not suitable for direct selection of transplastomic clones, but will confer resistance to plant cells when most genome copies have been altered. The coding region of the genes may be fused with AAD, NPTII or the BDH proteins, which are suitable for direct selection at the early stage of plastid transformation. Methods for protein fusion and suitable flexible linkers to link proteins encoded by the marker genes are described in Example 5. Selection for PPT resistance, gentamycin resistance or hygromycin resistance may be used to advantage at a later stage of plastid transformation when most plastid genome copies have been transformed.

The integrated marker gene sequences are subsequently removed by transiently expressing CRE, and selection for a negative marker, as described in Example 5. Transient expression of the site-specific recombinases, INT and CRE, will facilitate expression of agronomically important traits in the plastid genome of vegetatively propagated crops without the selectable marker gene.

REFERENCES

Adams D E, Bliska J B, Cozzarelli N R (1992) Cre-lox recombination in *Escherichia coli* cells. Mechanistic differences from the in vitro reaction. J Mol Biol 226:661-673

Aoyama T, Chua N H (1997) A glucocorticoid-mediated transcriptional induction system in transgenic plants. Plant Journal 11:605-612

Bendich A J (1987) Why do chloroplasts and mitochondria contain so many copies of their genome? Bioessays 6:279-282

Bock R (2001) Transgenic plastids in basic research and plant biotechnology. J Mol Biol 312:425-438

Bock R, Hermann M, Fuchs M (1997) Identification of critical nucleotide positions for plastid RNA editing site recognition. RNA 3:1194-1200

Carrer H, Hockenberry T N, Svab Z, Maliga P (1993) Kanamycin resistance as a selectable marker for plastid transformation in tobacco. Molecular & General Genetics 241: 49-56

Carrer H, Staub J M, Maliga P (1990) Gentamycin resistance in *Nicotiana* conferred by AAC(3)-I, a narrow substrate specificity acetyl transferase. Plant Mol Biol 17:301-303

Chaudhuri S, Maliga P (1996) Sequences directing C to U editing of the plastid psbL mRNA are located within a 22 nucleotide segment spanning the editing site. EMBO Journal 15:5958-5964

Chaudhuri S, Maliga P (1997) New insights into plastid RNA editing. Trends in Plant Science 2:5-6

Choi S, Begum D, Koshinsky H, Ow D W, Wing R A (2000) A new approach for the identification and cloning of genes: the pBACwich system using Cre/lox site-specific recombination. nucleic acids research 28:E19

Corneille S, Lutz K, Svab Z, Maliga P (2001) Efficient elimination of selectable marker genes from the plastid genome by the CRE-lox site-specific recombination system. Plant Journal 72:171-178

Craig N L (1988) The mechanism of conservative site-specific recombination. Annu Rev Genet 22:77-105

Dale E C, Ow D W (1990) Intra- and intermolecular site-specific recombination in plant cells mediated by bacteriophage P1 recombinase. Gene 91:79-85

Daniell H (1993) Foreign gene expression in chloroplasts of higher plants mediated by tungsten particle bombardment. Methods Enzymol 217:536-556

Daniell H, Datta R, Varma S, Gray S, Lee S B (1998) Containment of herbicide resistance through genetic engineering of the chloroplast genome. Nat Biotechnol 16:345-348

Daniell H, Muthukumar B, Lee S B (2001) Marker free transgenic plants: engineering the chloroplast genome without the use of antibiotic selection. Curr Genet 39:109-116

Day C D, Lee E, Kobayashi J, Holappa L D, Albert H, Ow D W (2000) Transgene integration into the same chromosome location can produce alleles that express at a predictable level, or alleles that are differentially silenced. Genes & Development 14:2869-2880

Gelvin S B, Schilperoort R A (1997) Plant Molecular Biology Manual. Kluwer Academic Publishers, Dordrecht Gleave A P, Mitra D S, Mudge S R, Morris B A (1999) Selectable marker-free transgenic plants without sexual crossing: transient expression of cre recombinase and use of a conditional lethal dominant gene. Plant Mol Biol 40:223-235

Golds T, Maliga P, Koop H U (1993) Stable plastid transformaton in PEG-treated protoplasts of *Nicotiana tabacum*. Biotechnology (N Y) 11:95-97

Grimsley N, Hohn B, Ramos C, Kado C, Rogowsky P (1989) DNA transfer from *Agrobacterium* to *Zea mays* or *Brassica* by agroinfection is dependent on bacterial virulence functions. Molecular and General Genetics 217:309-316

Gritz L, Davies J (1983) Plasmid-encoded hygromycin B resistance: the sequence of hygromycin B phosphotransferase gene and its expression in *Escherichia coli* and *Saccharomyces cerevisiae*. Gene 25:179-188

Groth A C, Olivares E C, Thyagarajan B, Calos M P (2000) A phage integrase directs efficient site-specific integration in human cells. Proc Natl Acad Sci USA 97:5995-6000

Guo F, Gopaul D N, Van Duyne G D (1997) Structure of Cre recombinase complexed with DNA in a site-specific recombination synapse. Nature 389:40-46

Hajdukiewicz P, Svab Z, Maliga P (1994) The small, versatile pPZP family of *Agrobacterium* binary vectors for plant transformation. Plant Mol Biol 25:989-994

Hajdukiewicz P T J, Gilbertson L, Staub J M (2001) Multiple pathways for Cre/lox-mediated recombination in plastids. Plant Journal 27:161-170

Heifetz P B (2000) Genetic engineering of the chloroplast. Biochimie 82:655-666

Heifetz P B, Tuttle A M (2001) Protein expression in plastids. Current Opinion in Plant Biology 4:157-161

Hoch B, Maier R M, Appel K, Igloi G L, Kössel H (1991) Editing of a chloroplast mRNA by creation of an initiation codon. Nature 353:178-180

Iamtham S, Day A (2000) Removal of antibiotic resistance genes from transgenic tobacco plastids. Nat Biotechnol 18:1172-1176

Kanevski I, Thakur S, Cosowsky L, Sunter G, Brough C, Bisaro D, Maliga P (1992) Tobacco lines with a high copy number of replicating recombinant geminivirus vectors after biolistic DNA delivery. The Plant Journal 2:457-463

Khan M S, Maliga P (1999) Fluorescent antibiotic resistance marker to track plastid transformation in higher plants. Nat Biotechnol 17:910-915

Knoblauch M, Hibberd J M, Gray J C, Van Bel A J E (1999) A galistan expansion femtosyringe for microinjection of eukaryotic organelles and prokaryotes. Nat Biotechnol 17:906-909

Koop H U, Steinmüller K, Wagner H, Rössler C, Eibl C, Sacher L (1996) Integration of foreign sequences into the tobacco plastome via PEG-mediated protoplast transformation. Planta 199:193-201

Kota M, Daniell H, Varma S, Garczynski S F, Gould F, Moar W J (1999) Overexpression of the *Bacillus thuringiensis* (Bt) Cry2Aa2 protein in chloroplasts confers resistance to plants against susceptible and Bt-resistant insects. Proc Natl Acad Sci USA 96:1840-1845

Kumagai M H, Donson J, della_Cioppa G, Grill L K (2000) Rapid, high-level expression of glycosylated rice alpha-amylase in transfected plants by an RNA viral vector. Gene 245:169-174

Kumagai M H, Donson J, della_Cioppa G, Harvey D, Hanley K, Grill L K (1995) Cytoplasmic inhibition of carotenoid biosynthesis with virus-derived RNA. Proc Natl Acad Sci USA 92:1679-1683

Kuroda H, Maliga P (2001a) Complementarity of the 16S rRNA penultimate stem with sequences downstream of the AUG destabilizes the plastid mRNAs. Nucleic Acids Research 29:970-975

Kuroda H, Maliga P (2001b) Sequences downstream of the translation initiation codon are important determinants of translation efficiency in chloroplasts. Plant Physiology 125:430-436

Lutz K A, Knapp J E, Maliga P (2001) Expression of bar in the plastid genome confers herbicide resistance. Plant Physiology 125:1585-1590

Lyznik L A, Rao K V, Hodges T K (1996) FLP-mediated recombination of FRT sites in the maize genome. Nucleic Acids Research 24:3784-3789

Maier R M, Zeltz P, Kossel H, Bonnard G, Gualberto J M, Grienenberger J M (1996) RNA editing in plant mitochondria and chloroplasts. Plant Mol Biol 32:343-365

Maliga P (1993) Towards plastid transformation in higher plants. Trends in Biotechnology 11:101-107

Maliga P (2002) Engineering the plastid genome of higher plants. Current Opinion in Plant Biology 5:164-172

Maliga P, Carrer H, Kanevski I, Staub J, Svab Z (1993) Plastid engineering in land plants: a conservative genome is open to change. Philosophical Transactions of the Royal Society of London—Series B: Biological Sciences 342:203-208

Maliga P, Klessig D F, Cashmore A R, Gruissem W, Varner J E (1995) Methods in Plant Molceular Biology. Cold Spring Harbor Laboratory Press, Cold Spring Harbor Martinez A, Sparks C, Hart C A, Thompson J, Jepson I (1999) Ecdysone agonist inducible transcription in transgenic tobacco plants. Plant Journal 19:97-106

McBride K E, Svab Z, Schaaf D J, Hogan P S, Stalker D M, Maliga P (1995) Amplification of a chimeric *Bacillus* gene in chloroplasts leads to an extraordinary level of an insecticidal protein in tobacco. Biotechnology (NY) 13:362-365

Moll B, Polsby L, Maliga P (1990) Streptomycin and lincomycin resistances are selective plastid markers in cultured *Nicotiana* cells. Molecular and General Genetics 221:245-250

Morris A C, Schaub T L, James A A (1991) FLP-mediated recombination in the vector mosquito, *Aedes aegypti*. Nucleic Acids Research 19:5895-5900

O'Neill C, Horvath G V, Horvath E, Dix P J, Medgyesy P (1993) Chloroplast transformation in plants: polyetylene glycol (PEG) treatment of protoplasts is an alternative to biolistic delivery systems. Plant Journal 3:729-738

Odell J, Caimi P, Sauer B, Russell S (1990) Site-directed recombination in the genome of transgenic tobacco. Molecular And General Genetics 223:369-378

Onouchi H, Nishihama R, Kudo M, Machida Y, Machida C (1995) Visualization of site-specific recombination catalyzed by a recombinase from *Zygosaccharomyces rouxii* in *Arabidopsis thaliana*. Molecular and General Genetics 247:653-660

Onouchi H, Yokoi K, Machida C, Matsuzaki H, Oshima Y, Matsuoka K, Nakamura K, Machida Y (1991) Operation of an efficient site-specific recombination system of *Zygosaccharomyces rouxii* in tobacco cells. Nucleic Acids Research 19:6373-6378

Ow D W (2001) The right chemistry for marker gene removal? Nat Biotechnol 19:115-116

Peele C, Jordan C V, Muangsan N, Turnage M, Egelkrout E, Eagle P, Hanley_Bowdoin L, Robertson D (2001) Silencing of a meristematic gene using geminivirus-derived vectors. Plant Journal 27:357-366

Potrykus I, Spangenberg G (1995) Gene transfer to plants. Springer-Verlag, Berlin Ratcliff F, Martin_Hernandez A M, Baulcombe D C (2001) Technical Advance. Tobacco rattle virus as a vector for analysis of gene function by silencing. Plant Journal 25:237-245

Rommens C M, Salmeron J M, Baulcombe D C, Staskawicz B J (1995) Use of a gene expression system based on potato virus X to rapidly identify and characterize a tomato Pto homolog that controls fenthion sensitivity. Plant Cell 7:249-257

Ruf S, Hermann M, Berger I J, Carrer H, Bock R (2001) Stable genetic transformation of tomato plastids: foreign protein expression in fruit. Nat Biotechnol 19:870-875

Serino G, Maliga P (1997) A negative selection scheme based on the expression of cytosine deaminase in plastids. Plant Journal 12:697-701

Sidorov V A, Kasten D, Pang S Z, Hajdukiewicz P T J, Staub J M, Nehra N S (1999) Stable chloroplast transformation in potato: use of green fluorescent protein as a plastid marker. Plant Journal 19:209-216

Sikdar S R, Serino G, Chaudhuri S, Maliga P (1998) Plastid transformation in *Arabidopsis thaliana*. Plant Cell Reports 18:20-24

Staub J M, Garcia B, Graves J, Hajdukiewicz P T J, Hunter P, Nehra N, Paradkar V, Schlittler M, Carroll J A, Ward D, Ye G, Russell D A (2000) High-yield production of a human therapeutic protein in tobacco chloroplasts. Nat Biotechnol 18:333-338

Staub J M, Maliga P (1993) Accumulation of D1 polypeptide in tobacco plastids is regulated via the untranslated region of the psbA mRNA. EMBO Journal 12:601-606

Staub J M, Maliga P (1994a) Extrachromosomal elements in tobacco plastids. Proc Natl Acad Sci USA 91:7468-7472

Staub J M, Maliga P (1994b) Translation of psbA mRNA is regulated by light via the 51'-untranslated region in tobacco plastids. Plant Journal 6:547-553

Staub J M, Maliga P (1995) Marker Rescue From the *Nicotiana Tabacum* Plastid Genome Using a Plastid *Escherichia Coli* Shuttle Vector. Molecular & General Genetics 249:37-42

Sugiura M (1992) The Chloroplast Genome. Plant Mol Bio 19:149-168

Svab Z, Hajdukiewicz P, Maliga P (1990) Stable transformation of plastids in higher plants. Proc Natl Acad Sci USA 87:8526-8530

Svab Z, Maliga P (1993) High-frequency plastid transformation in tobacco by selection for a chimeric aadA gene. Proc Natl Acad Sci USA 90:913-917

Thomason L C, Calendar R, Ow D W (2001) Gene insertion and replacement in *Schizosaccharomyces pombe* mediated by the *Streptomyces* bacteriophage phiC31 site-specific recombination system. 265:1031-1038

Thorpe H M, Smith M C (1998) In vitro site-specific integration of bacteriophage DNA catalyzed by a recombinase of the resolvase/invertase family. Proc Natl Acad Sci USA 95:5505-5510

Thorpe H M, Wilson S E, Smith M C M (2000) Control of directionality in the site-specific recombination system of the *Streptomyces* phage phiC31. Molecular Microbiology 38:232-241

Thyagarajan B (2001) Site-specific genomic integration in mammalian cells mediated by phage phiC31 integrase. Molecular & Cellular Biology 21:3926-3934

Timko M P, Kaush A P, Hand J M, Cashmore A R (1985) Structure and expression of nuclear genes encoding polypeptides of the photosynthetic apparatus. In: Steinback K E, Bonitz S, Arntzen C J, Bogorad L (eds) *Molecular biology of the photosynthetic apparatus*, Cold Spring Harbor Laboratory, Cold Spring Harbor, pp 381-396 .

van Haaren M J, Ow D W (1993) Prospects of applying a combination of DNA transposition and site-specific recombination in plants: a strategy for gene identification and cloning. Plant Mol Biol 23:525-533

Wilkinson C J, Hughes-Thomas, Z. A., Martin, C. J., Bohm, I., Mironenko, T., Deacon, M., Wheatcroft, M., Wirtz, G., Staunton, J. and Leadlay, P. F. (2002) Increasing the efficiency of heterologous promoters in actinomycetes. Journal of Molecular Microbiology and Biotechnology In Press Ye G N, Hajdukiewicz P T J, Broyles D, Rodriquez D, Xu C W, Nehra N, Staub J M (2001) Plastid-expressed 5-enolpyruvylshikimate-3-phosphate synthase genes provide high level glyphosate tolerance in tobacco. Plant Journal 25:261-270

Zoubenko O V, Allison L A, Svab Z, Maliga P (1994) Efficient targeting of foreign genes into the tobacco plastid genome. Nucleic Acids Research 22:3819-3824

Zuo J, Chua N H (2000) Chemical-inducible systems for regulated expression of plant genes. Current Opinion in Biotechnology 11:146-151

Zuo J, Niu Q W, Chua N H (2000) An estrogen receptor-based transactivator XVE mediates highly inducible gene expression in transgenic plants. Plant Journal 24:265-273

Haldrup A, Petersen S G, Okkels F T (1998) The xylose isomerase gene from *Thermoanaerobacterium thermosulfurogenes* allows effective selection of transgenic plant cells using D-xylose as the selection agent. Plant Mol Biol 37:287-296

Joersboro M, Donaldson I, Kreiberg J, Peterson S G, Brunstedt, J., Okkels F T (1998) Analysis of mannose selection used for transformation of sugar beet. Molecular Breeding 4:111-117

Negrotto D, Jolley M, Beer S, Wenck A R (2000) The use of phosphomannose isomerase as a selectable marker to recover transgenic maize plants. Plant Cell Rep 19:798-803

Appendix I

The following sequences were utilized in practicing the methods of the present invention.

```
Seq. ID No. 1 lox site (BglII-HindIII)
AGATCTATAACTTCGTATAATGTATGCTATACGAAGTTATAAG

CTT

Seq. ID No. 2 lox site (KpnI-BglII)
GGTACCATAACTTCGTATAATGTATGCTATACGAAGTTATAGA

TCT

Seq. ID No. 3 attB sequence (PstI-SpeI)
CTGCAGCCGCGGTGCGGGTGCCAGGGCGTGCCCTTGGGCTCCC

CGGGCGCGTACTCCACTAGT

Seq. ID No. 4 pSAC113 (KpnI-SacI)
GGTACCATAACTTCGTATAATGTATGCTATACGAAGTTATAGA

TCAGCTTGCATGCCTGCAGGTCGAATATAGCTCTTCTTTCTTA

TTTCAATGATATTATTATTTCAAAGATAAGAGATATTCAAAGA

TAAGAGATAAGAAGAAGTCAAAATTTGATTTTTTTTTGGAAA

AAAAAAATCAAAAAGATATAGTAACATTAGCAAGAAGAGAAAC

AAGTTCTATTTCACAATTTAAACAAATACAAAATCAAAATAGA

ATACTCAATCATGAATAAATGCAAGAAAATAACCTCTCCTTCT

TTTTCTATAATGTAAACAAAAAAGTCTATGTAAGTAAAATACT

AGTAAATAAATAAAAAGAAAAAAAGAAAGGAGCAATAGCACCC

TCTTGATAGAACAAGAAAATGATTATTGCTCCTTTCTTTTCAA

AACCTCCTATAGACTAGGCCAGGATCGCTCTAGACATTATTTG

CCGACTACCTTGGTGATCTCGCCTTTCACGTAGTGGACAAATT

CTTCCAACTGATCTGCGCGCGAGGCCAAGCGATCTTCTTCTTG

TCCAAGATAAGCCTGTCTAGCTTCAAGTATGACGGGCTGATAC

TGGGCCGGCAGGCGCTCCATTGCCCAGTCGGCAGCGACATCCT

TCGGCGCGATTTTGCCGGTTACTGCGCTGTACCAAATGCGGGA

CAACGTAAGCACTACATTTCGCTCATCGCCAGCCCAGTCGGGC

GGCGAGTTCCATAGCGTTAAGGTTTCATTTAGCGCCTCAAATA

GATCCTGTTCAGGAACCGGATCAAAGAGTTCCTCCGCCGCTGG

ACCTACCAAGGCAACGCTATGTTCTCTTGCTTTTGTCAGCAAG

ATAGCCAGATCAATGTCGATCGTGGCTGGCTCGAAGATACCTG

CAAGAATGTCATTGCGCTGCCATTCTCCAAATTGCAGTTCGCG

CTTAGCTGGATAACGCCACGGAATGATGTCGTCGTGCACAACA

ATGGTGACTTCTACAGCGCGGAGAATCTCGCTCTCTCCAGGGG

AAGCCGAAGTTTCCAAAAGGTCGTTGATCAAAGCTCGCCGCGT

TGTTTCATCAAGCCTTACGGTCACCGTAACCAGCAAATCAATA

TCACTGTGTGGCTTCAGGCCGCCATCCACTGCGGAGCCGTACA

AATGTACGGCCAGCAACGTCGGTTCGAGATGGCGCTCGATGAC

GCCAACTACCTCTGATAGTTGAGTCGATACTTCGGCGATCACC

GCTTCCCCCATGGATCCCTCCCTACAACTGTATCCAAGCGCTT

CGAATTCGCCCGGAGTTCGCTCCCAGAAATATAGCCATCCCTG

CCCCCTCACGTCAATCCCACGAGCCTCTTATCCATTCTCATTG

AACGACGGCGGGGAGCGGATCTATAACTTCGTATAATGTATG

CTATACGAAGTTATAAGCTTGATATCGAATTCCTGCAGCCGCG

GTGCGGGTGCCAGGGCGTGCCCTTGGGCTCCCCGGGCGCGTAC

TCCACTAGTTCTAGAGCGGCCGCCACCGCGGTGGAGCTC

Seq. ID No. 5
int coding region (BamHI-XbaI)
GGATCCATGGCTAGCGACACGTACGCGGGTGCTTACGACCGTC

AGTCGCGCGAGCGCGAAAATTCGAGCGCAGCAAGCCCAGCGAC

ACAGCGTAGCGCCAACGAAGACAAGGCGGCCGACCTTCAGCGC

GAAGTCGAGCGCGACGGGGGCCGGTTCAGGTTCGTCGGGCATT

TCAGCGAAGCGCCGGGCACGTCGGCGTTCGGGACGGCGGAGCG

CCCGGAGTTCGAACGCATCCTGAACGAATGCCGCGCCGGGCGG
```

-continued
CTCAACATGATCATTGTCTATGACGTGTCGCGCTTCTCGCGCC
TGAAGGTCATGGACGCGATTCCGATTGTCTCGGAATTGCTCGC
CCTGGGCGTGACGATTGTTTCCACTCAGGAAGGCGTCTTCCGG
CAGGGAAACGTCATGGACCTGATTCACCTGATTATGCGGCTCG
ACGCGTCGCACAAAGAATCTTCGCTGAAGTCGGCGAAGATTCT
CGACACGAAGAACCTTCAGCGCGAATTGGGCGGGTACGTCGGC
GGGAAGGCGCCTTACGGCTTCGAGCTTGTTTCGGAGACGAAGG
AGATCACGCGCAACGGCCGAATGGTCAATGTCGTCATCAACAA
GCTTGCGCACTCGACCACTCCCCTTACCGGACCCTTCGAGTTC
GAGCCCGACGTAATCCGTGGTGGTGGCGTGAGATCAAGACGC
ACAAACACCTTCCCTTCAAGCCGGGCAGTCAAGCCGCCATTCA
CCCGGGCAGCATCACGGGCTTTGTAAGCGCATGGACGCTGAC
GCCGTGCCGACCCGGGGCGAGACGATTGGGAAGAAGACCGCTT
CAAGCGCCTGGGACCCGGCAACCGTTATGCGAATCCTTCGGGA
CCCGCGTATTGCGGGCTTCGCCGCTGAGGTGATCTACAAGAAG
AAGCCGGACGGCACGCCGACCACGAAGATTGAGGGTTACCGCA
TTCAGCGCGACCCGATCACGCTCCGGCCGGTCGAGCTTGATTG
CGGACCGATCATCGAGCCCGCTGAGTGGTATGAGCTTCAGGCG
TGGTTGGACGGCAGGGGGCGCGGCAAGGGGCTTTCCCGGGGGC
AAGCCATTCTGTCCGCCATGGACAAGCTGTACTGCGAGTGTGG
CGCCGTCATGACTTCGAAGCGCGGGGAAGAATCGATCAAGGAC
TCTTACCGCTGCCGTCGCCGGAAGGTGGTCGACCCGTCCGCAC
CTGGGCAGCACGAAGGCACGTGCAACGTCAGCATGGCGGCACT
CGACAAGTTCGTTGCGGAACGCATCTTCAACAAGATCAGGCAC
GCCGAAGGCGACGAAGAGACGTTGGCGCTTCGTGGGAAGCCG
CCCGACGCTTCGGCAAGCTCACTGAGGCGCCTGAGAAGAGCGG
CGAACGGGCGAACCTTGTTGCGGAGCGCGCCGACGCCCTGAAC
GCCCTTGAAGAGCTGTACGAAGACCGCGCGGCAGGCGCGTACG
ACGGACCCGTTGGCAGGAAGCACTTCCGGAAGCAACAGGCAGC
GCTGACGCTCCGGCAGCAAGGGGCGGAAGAGCGGCTTGCCGAA
CTTGAAGCCGCCGAAGCCCCGAAGCTTCCCCTTGACCAATGGT
TCCCCGAAGACGCCGACGCTGACCCGACCGGCCCTAAGTCGTG
GTGGGGCGCGCGTCAGTAGACGACAAGCGCGTGTTCGTCGGG
CTCTTCGTAGACAAGATCGTTGTCACGAAGTCGACTACGGGCA
GGGGGCAGGGAACGCCCATCGAGAAGCGCGCTTCGATCACGTG
GGCGAAGCCGCCGACCGACGACGACGAAGACGACGCCCAGGAC
GGCACGGAAGACGTAGCGGCGTAGTCTAGA Seq. ID No. 6 attP sequence (XhoI-HindIII)
CTCGAGCAATCGCCCTGGGTGGGTTACACGACGCCCCTCTATG
GCCCGTACTGACGGACACACCGAAGCCCCGGCGGCAACCCTCA
GCGGATGCCCCGGGGCTTCACGTTTTCCCAGGTCAGAAGCGGT
TTTCGGGAGTAGTGCCCCAACTGGGGTAACCTTTGAGTTCTCT
CAGTTGGGGGCGTAGGGTCGCCGACATGACACAAGGGGTTGTG
ACCGGGAAGCTT Seq. ID No. 7 pKO103 (AhdI-SacI)
CCACCGCGGTGGCGGCCGCTCTAGAACTAGTGGATCCCCCGGG
CTGCAGGAATTCGATATCAAGCTTATCGATACCGTCGACAGAT
CTATAACTTCGTATAGCATACATTATACGAAGTTATGATCAAG
CTAGCTTGCTAGATTTTGTATTTCAAATCTTGTATATCTAGGT
AAGTATATHNDACTTAGTCAAAATATATGCAATAGAATCTTTG
TTGTATTCGGCTCAATCCTTTTAGTAAAAGATTGGGCCGAGTT
TAATTGCAATTCAATTAAGAGAACGAAGGATAATTACTTGAGT
TCTTTCTCCTTATCCTTCTTTATTTCCTGCTAATTTATCTGCT
AATGTCTACTCTAGCTACACCCGCTCAGAAGAACTCGTCAAGA
TVAGGCGATAGAAGGCGATGCGCTGCGAATCGGGAGCGGCGAT
ACCGTAAAGCACGAGGAAGCGGTCAGCCCATTCGCCGCCAAGC
TCTTCAGCAATATCACGGGTAGCCAACGCTATGTCCTGATAGC
GGTCCGCCACACCCAGCCGGCCACAGTCGATGAATCCAGAAAA
GCGGCCATTTTCCACCATGATATTCGGCAAGCAGGCATCGCCA
TGTGTCACGACGAGATCCTCGCCGTCGGGCATGCGCGCCTTGA
GCCTGGCGAACAGTTCGGCTGGCGCGAGCCCCTGATGCTCTTC
GTCCAGATCATCCTGATCGACAAGACCGGCTTCCATCCGAGTA
CGTGCTCGCTCGATGCGATGTTTCGCTTGGTGGTCGAATGGGC
AGGTAGCCGGATCAAGCGTATGCAGCCGCCGCATTGCATCAGC
CATGATGGATACTTTCTCGGCAGGAGCAAGGTGAGATGACAGG
AGATCCTGCCCCGGCACTTCGCCCAATAGCAGCCAGTCCCTTC
CCGCTTCAGTGACAACGTCGAGCACAGCTGCGCAAGGAACGCC
CGTCGTGGCCAGCCACGATAGCCGCGCTGCCTCGTCCTGGAGT
TCATTCAGGGCACCGGACAGGTCGGTCTTGACAAAAAGAACCG
GGCGCCCCTGCGCTGACAGCCGGAACACGCGGCATCAGAGCA
GCCGATTGTCTGTTGTGCCCAGTCATAGCCGAATAGCCTCTCC
ACCCAAGCGGCCGGAGAACTGCGTGCAATCCATCTTGTTCAA
TGCTAGCCGTGGAAACCCCAGAACCAGADNAGTAGTAGGATTG
ATTCTCATAATAATAAAATAAATAAATATGTCGAAATGTTTTT
GCAAAATTATCGAATTTAAAATAAATGTCCGCTTGCACGTCG
ATCGGTTAATTCTCCCAGAAATATAGCCATCCCTGCCCCCTCA
CGTCAATCCCACGAGCCTCTTATCCATTCTCATTGAACGACGG
CGGGGGAGCGAGCTTCCCGGTCACAACCCCTTGTGTCATGTCG
GCGACCCTACGCCCCAACTGAGAGAACTCAAAGGTTACCCCA
GTTGGGGCACTACTCCCGAAAACCGCTTCTGACCTGGGAAAAC
GTGAAGCCCCGGGGCATCCGCTGAGGGTTGCCGCCGGGGCTTC
GGTGTGTCCGTCAGTACGGGCCATAGAGGGGCGTCGTGTAACC -continued

CACCCAGGGCGATTGCTCGACCAGCTTTTGTTCCCTTTAGTGA

GGGTTAATTGCGCGCTTGGCGTAATCATGGTCATAGCTGTTTC

CTGTGTGAAATTGTTATCCGCTCACAATTCCACACAACATACG

AGCCGGAAGCATAAAGTGTAAAGCCTGGGGTGCCTAATGAGTG

AGCTAACTCACATTAATTGCGTTGCGCTCACTGCCCGCTTTCC

AGTCGGGAAACCTGTCGTGCCAGCTGCATTAATGAATCGGCCA

ACGCGCGGGAGAGGCGGTTTGCGTATTGGGCGCTCTTCCGCT

TCCTCGCTCACTGACTCGCTGCGCTCGGTCGTTCGGCTGCGG

GAGCGGTATCAGCTCACTCAAAGGCGGTAATACGGTTATCCAC

AGAATCAGGGGATAACGCAGGAAAGAACATGTGAGCAAAAGGC

CAGCAAAAGGCCAGGAACCGTAAAAAGGCCGCGTTGCTGGCGT

TTTTCCATAGGCTCCGCCCCCCTGACGAGCATCACAAAAATCG

ACGCTCAAGTCAGAGGTGGCGAAACCCGACAGGACTATAAAGA

TACCAGGCGTTTCCCCCTGGAAGCTCCCTCGTGCGCTCTCCTG

TTCCGACCCTGCCGCTTACCGGATACCTGTCCGCCTTTCTCCC

TTCGGGAAGCGTGGCGCTTTCTCATAGCTCACGCTGTAGGTAT

CTCAGTTCGGTGTAGGTCGTTCGCTCCAAGCTGGGCTGTGTGC

ACGAACCCCCCGTTCAGCCCGACCGCTGCGCCTTATCCGGTAA

CTATCGTCTTGAGTCCAACCCGGTAAGACACGACTTATCGCCA

CTGGCAGCAGCCACTGGTAACAGGATTAGCAGAGCGAGGTATG

TAGGCGGTGCTACAGAGTTCTTGAAGTGGTGGCCTAACTACGG

CTACACTAGAAGGACAGTATTTGGTATCTGCGCTCTGCTGAAG

CCAGTTACCTTCGGAAAAAGAGTTGGTAGCTCTTGATCCGGCA

AACAAACCACCGCTGGTAGCGGTGGTTTTTTTGTTTGCAAGCA

GCAGATTACGCGCAGAAAAAAAGGATCTCAAGAAGATCCTTTG

ATCTTTTCTACGGGGTCTGACGCTCAGTGGAACGAAAACTCAC

GTTAAGGGATTTTGGTCATGAGATTATCAAAAAGGATCTTCAC

CTAGATCCTTTTAAATTAAAAATGAAGTTTTAAATCAATCTAA

AGTATATATGAGTAAACTTGGTCTGACAGTTACCAATGCTTAA

TCAGTGAGGCACCTATCTCAGCGATCTGTCTATTTCGTTCATC

CATAGTTGCCTGACTCC

Seq. ID No. 8 attL sequence
AGCCGCGGTGCGGGTGCCAGGGCGTGCCCTTGAGTTCTCTCAG

TTGGGGGCGTAGGGTCGCCGACATGACACAAGGGGTTGTGACC

GGG

Seq. ID No. 9 attR sequence
GAGCAATCGCCCTGGGTGGGTTACACGACGCCCCTCTATGGCC

CGTACTGACGGACACACCGAAGCCCCGGCGGCAACCCTCAGCG

GATGCCCCGGGGCTTCACGTTTTCCCAGGTCAGAAGCGGTTTT

CGGGAGTAGTGCCCCAACTGGGGTAACCTTTGGGCTCCCCGGG

CGCGTACTCCAC

-continued

Seq. ID No. 10 loxdel1T
5'-GGTACCATAACTTCGTATAATGTATGCTATACGAAGTTAT

AGATCT-3'

Seq. ID No. 11 loxdel1L
5'-AGATCTATAACTTCGTATAGCATACATTATACGAAGTTAT

GGTACC-3'

Seq. ID No. 12 loxdel2T
5'-AGATCTATAACTTCGTATAATGTATGCTATACGAAGTTAT

AAGCTT-3'

Seq. ID No. 13 loxdel2L
5'-AAGCTTATAACTTCGTATAGCATACATTATACGAAGTTAT

AGATCT-3'

Seq. ID No. 14 attBPstI
5'-CTGCAGCCGCGGTGCGGGTGCCAGGGCGTGCCCTTGGGCT

CCCCGGGCGCGTACTCCACTAGT-3'

Seq. ID No. 15 attBSpeI
5'-ACTAGTGGAGTACGCGCCCGGGGAGCCCAAGGGCACGCCC

TGGCACCCGCACCGCGGCTGCAG-3'

Seq. ID No. 16 attPXhoI
5'-CAACTCGAGCAATCGCCCTGGGTG-3'

Seq. ID No. 17 attPHindIII
5'-CAAAAGCTTCCCGGTCACAACCCCTTG-3'

Seq. ID No. 18 Primer 136
5'-CCGCCAGCGTTCATCCTGAGC-3'

Seq. ID No. 19 neoAL
5'-TGACAGCCGGAACACGGCGGC-3'

Seq. ID No. 20 neoAU
5'-TGAAGAGCTTGGCGGCGAAT-3'

Seq. ID No. 21 Primer 191
5'-GAGATGTAACTCCAGTTCC-3'

Seq. ID No. 22; 16-mer junction peptide
5'-GAACTTGTTGAAGGAAAATTGGAGCTAGTAGAAGGTCTTA

AAGTCGCC-3'

Seq. ID No. 23; 10-mer junction peptide
5'-GAACTTGCAGTTGAAGGAAAATTGGAGGCC-3'.

Seq. ID No. 24 Plastid hph sequence
ccATGgctag cAAAAAGCCT GAACTCACCG CGACGTCTGT

CGAGAAGTTT CTGATCGAAA AGTTCGACAG CGTCTCCGAC

CTGATGCAGC TCTCGGAGGG CGAAGAATCT CGTGCTTTCA

GCTTCGATGT AGGAGGGCGT GGATATGTCC TGCGGGTAAA

TAGCTGCGCC GATGGTTTCT ACAAAGATCG TTATGTTTAT

CGGCACTTTG CATCGGCCGC GCTCCCGATT CCGGAAGTGC

TTGACATTGG GGAATTtAGC GAGAGCCTGA CCTATTGCAT

CTCCCGCCGT GCACAGGGTG TCACGTTGCA AGACCTGCCT

GAAACCGAAC TGCCCGCTGT TCTGCAGCCG GTCGCGGAGG

CtATGGATGC GATCGCTGCG GCCGATCTTA GCCAGACGAG

CGGGTTCGGC CCATTCGGAC CGCAAGGAAT CGGTCAATAC

ACTACATGGC GTGATTTCAT ATGCGCGATT GCTGATCCCC

```
ATGTGTATCA CTGGCAAACT GTGATGGACG ACACCGTCAG
TGCGTCCGTC GCGCAGGCTC TCGATGAGCT GATGCTTTGG
GCCGAGGACT GCCCCGAAGT CCGGCACCTC GTGCACGCGG
ATTTCGGCTC CAACAATGTC CTGACGGACA ATGGCCGCAT
AACAGCGGTC ATTGACTGGA GCGAGGCGAT GTTCGGGGAT
TCCCAATACG AGGTCGCCAA CATCTTCTTC TGGAGGCCGT
GGTTGGCTTG TATGGAGCAG CAGACGCGCT ACTTCGAGCG
GAGGCATCCG GAGCTTGCAG GATCGCCGCG GCTCCGGGCG
TATATGCTCC GCATTGGTCT TGACCAACTC TATCAGAGCT
TGGTTGACGG CAATTTCGAT GATGCAGCTT GGGCGCAGGG
TCGATGCGAC GCAATCGTCC GATCCGGAGC CGGGACTGTC
GGGCGTACAC AAATCGCCCG CAGAAGCGCG GCCGTCTGGA
CCGATGGCTG TGTAGAAGTA CTCGCCGATA GTGGAAACCG
ACGCCCCAGC ACTCGTCCtc GaGCAAAGGA ATAGatctag
a Seq. ID No. 25.
Int gene in plasmid pKO107 (SacI-HindIII)
gagctcggta ccGCTCCCCC GCCGTCGTTC AATGAGAATG
GATAAGAGGC TCGTGGGATT GACGTGAGGG GGCAGGGATG
GCTATATTTC TGGGAGCGAA CTCCGGGCGA ATcGAAGCG
CtTGGATACA GTTGTAGGGA GGGATCCATG GCTAGCgaca
cgtacgcggg tgcttacgac cgtcagtcgc gcgagcgcga
Aaattcgagc gcagcaagcc cagcgacaca gcgtagcgcc
aacgaagaca aggcggccga ccttcagcgc gaagtcgagc
gcgacggggg ccggttcagg ttcgtcgggc atttcagcga
agcgccgggc acgtcggcgt tcgggacggg ggagcgcccg
gagttcgaac gcatcctgaa cgaatgccgc gccgggcggc
tcaacatgat cattgtctat gacgtgtcgc gcttctcgcg
cctgaaggtc atggacgcga ttccgattgt ctcggaattg
ctcgccctgg gcgtgacgat tgtttccact caggaaggcg
tcttccggca gggaaacgtc atggacctga ttcacctgat
tatgcggctc gacgcgtcgc acaaagaatc ttcgctgaag
tcggcgaaga ttctcgacac gaagaaccct cagcgcgaat
tgggcgggta cgtcggcggg aaggcgcctt acggcttcga
gcttgtttcg gagacgaagg agatcacgcg caacgccga
atggtcaatg tcgtcatcaa caagcttgcg cactcgacca
ctcccttac cggacccttc gagttcgagc ccgacgtaat
ccggtggtgg tggcgtgaga tcaagacgca caaacacctt
cccttcaagc cgggcagtca agccgccatt caccccgggca
gcatcacggg gctttgtaag cgcatggacg ctgacgccgt
gccgacccgg ggcgagacga ttgggaagaa gaccgcttca
```

```
agcgcctggg acccggcaac cgttatgcga atccttcggg
acccgcgtat tgcgggcttc gccgctgagg tgatctacaa
gaagaagccg gacggcacgc cgaccacgaa gattgagggt
taccgcattc agcgcgaccc gatcacgctc cggccggtcg
agcttgattg cggaccgatc atcgagcccg ctgagtggta
tgagcttcag gcgtggttgg acggcagggg gcgcggcaag
gggctttccc ggggcaagc cattctgtcc gccatggaca
agctgtactg cgagtgtggg gccgtcatga cttcgaagcg
cggggaagaa tcgatcaagg actcttaccg ctgccgtcgc
cggaaggtgg tcgacccgtc cgcacctggg cagcacgaag
gcacgtgcaa cgtcagcatg gcggcactcg acaagttcgt
tgcggaacgc atcttcaaca agatcaggca cgccgaaggc
gacgaagaga cgttggcgct tctgtgggaa gccgcccgac
gcttcggcaa gctcactgag gcgcctgaga gagcggcga
acgggcgaac cttgttgcgg agcgcgccga cgccctgaac
gcccttgaag agctgtacga agaccgcgcg gcaggcgcgt
acgacggacc cgttggcagg aagcacttcc ggaagcaaca
ggcagcgctg acgctccggc agcaagggc ggaagagcgg
cttgccgaac ttgaagccgc cgaagcccg aagcttcccc
ttgaccaatg gttccccgaa gacgccgacg ctgacccgac
cggccctaag tcgtggtggg ggcgcgcgtc agtagacgac
aagcgcgtgt tcgtcgggct cttcgtagac aagatcgttg
tcacgaagtc gactacgggc agggggcagg gaacgcccat
cgagaagcgc gcttcgatca cgtgggcgaa gccgccgacc
gacgacgacg aagacgacgc ccaggacggc acggaagacg
tagcggcgta gTctagaGCG ATCCTGGCCT AGTCTATAGG
AGGTTTTGAA AAGAAAGGAG CAATAATCAT TTTCTTGTTC
TATCAAGAGG GTGCTATTGC TCCTTTCTTT TTTTCTTTTT
ATTTATTTAC TAGTATTTTA CTTACATAGA CTTTTTTGTT
TACATTATAG AAAAAGAAGG AGAGGTTATT TTCTTGCATT
TATTCATGAT TGAGTATTCT ATTTTGATTT TGTATTTGTT
TAAATTGTGA AATAGAACTT GTTTCTCTTC TTGCTAATGT
TACTATATCT TTTTGATTTT TTTTTTCCAA AAAAAAATC
AAATTTTGAC TTCTTCTTAT CTCTTATCTT TGAATATCTC
TTATCTTTGA AATAATAATA TCATTGAAAT AAGAAAGAAG
AGCTATATTC GAcctgcagg catgcaagct t Seq. ID No. 26. Edited
Int gene in plasmid pKO111 (SacI-HindII)
gagctcggta cccaaaGCTC CCCCGCCGTC GTTCAATGAG
AATGGATAAG AGGCTCGTGG GATTGACGTG AGGGGGCAGG
GATGGCTATA TTTCTGGGAG CGAACTCCGG GCGAATACGA
```

-continued
```
AGCGCTTGGA TACAGTTGTA GGGAGGGATC CATGGCTAGC gacacgtacg cgggtgctta cgaccgtcag tcgcgcgagc gcgaAaattc gagcgcagca agcccagcga cacagcgtag cgccaacgaa gacaaggcgg ccgaccttca gcgcgaagtc gagcgcgacg ggggccggtt caggttcgtc gggcatttca gcgaagcgcc gggcacgtcg gcgttcggga cggcggagcg cccggagttc gaacgcatcc tgaacgaatg ccgcgccggg cggctcaaca tgatcattgt ctatgacgtg tcgcgcttct cgcgcctgaa ggtcatggac gcgattccga ttgtctcgga attgctcgcc ctgggcgtga cgattgtttc cactcaggaa ggcgtcttcc ggcagggaaa cgtcatggac ctgattcacc tgattatgcg gctcgacgcg tcgcacaaag aatcttcgct gaagtcggcg aagattctcg acacgaagaa ccttcagcgc gaattgggcg gtacgtcgg cgggaaggcg ccttacggct tcgagcttgt ttcggagacg aaggagatca cgcgcaacgg ccgaatggtc aatgtcgtca tcaacaagct tgcgcactcg accactcccc ttaccggacc cttcgagttc gagcccgacg taatccggtg gtggtggcgt gagatcaaga cgcacaaaca ccttcccttc aagccgggca gtcaagccgc cattcacccg ggcagcatca cggggctttg taagcgcatg gacgctgacg ccgtgccgac ccggggcgag acgattggga agaagaccgc ttcaagcgcc tgggacccgg caaccgttat gcgaatcctt cgggacccgc gtattgcggg cttcgccgct gaggtgatct acaagaagaa gccggacggc acgccgacca cgaagattga gggttaccgc attcagcgcg acccgatcac gctccggccg gtcgagcttg attgcggacc gatcatcgag cccgctgagt ggtatgagct tcaggcgtgg ttggacggca gggggcgcgg caaggggctt tcccgggggc aagccattct gtccgccatg gacaagctgt actgcgagtg tggcgccgtc atgacttcga agcgcgggga agaatcgatc aaggactctt accgctgccg tcgccggaag gtggtcgacc cgtccgcacc tgggcagcac gaaggcacgt gcaacgtcag catggcggca ctcgacaagt tcgttgcgga acgcatcttc aacaagatca ggcacgccga aggcgacgaa gagacgttgg cgcttctgtg ggaagccgcc cgacgcttcg gcaagctcac tgaggcgcct gagaagagcg gcgaacgggc gaaccttgtt gcggagcgcg ccgacgccct gaacgccctt gaagagctgt acgaagaccg cgcggcaggc gcgtacgacg gacccgttgg caggaagcac ttccggaagc aacaggcagc gctgacgctc cggcagcaag gggcggaaga gcggcttgcc gaacttgaag ccgccgaagc cccgaagctt
```

```
ccccttgacc aatggttccc cgaagacgcc gacgctgacc cgaccggccc taagtcgtgg tgggggcgcg cgtcagtaga cgacaagcgc gtgttcgtcg ggctcttcgt agacaagatc gttgtcacga agtcgactac gggcaggggg cagggaacgc ccatcgagaa gcgcgcttcg atcacgtggg cgaagccgcc gaccgacgac gacgaagacg acgcccagga cggcacggaa gacgtagcgg cgtagTctag aGAAATTCAA TTAAGGAAAT

AAATTAAGGA AATACAAAAA GGGGGGTAGT CATTTGTATA

TAACTTTGTA TGACTTTTCT CTTCTATTTT TTTGTATTTC

CTCCCTTTCC TTTTCTATTT GTATTTTTTT ATCATTGCTT

CCATTGAATT aattcatgca agctt

Seq. ID. No. 27
Plastid targeted nuclear int gene
in Agrobacterium binary vector pKO117
GAATTCATTT TCACGTGTGG AAGATATGAA TTTTTTTGAG

AAACTAGATA AGATTAATGA ATATCGGTGT TTTGGTTTTT

TCTTGTGGCC GTCTTTGTTT ATATTGAGAT TTTTCAAATC

AGTGCGCAAG ACGTGACGTA AGTATCTGAG CTAGTTTTTA

TTTTTCTACT AATTTGGTCG TTTATTTCGG CGTGTAGGAC

ATGGCAACCG GGCCTGAATT TCGCGGGTAT TCTGTTTCTA

TTCCAACTTT TTCTTGATCC GCAGCCATTA ACGACTTTTG

AATAGATACG CTGACACGCC AAGCCTCGCT AGTCAAAAGT

GTACCAAACA ACGCTTTACA GCAAGAACGG AATGCGCGTG

ACGCTCGCGG TGACGCCATT TCGCCTTTTC AGAAATGGAT

AAATAGCCTT GCTTCCTATT ATATCTTCCC AAATTACCAA

TACATTACAC TAGCATCTGA ATTTCATAAC CAATCTCGAT

ACACCAAATC GATaggatcc AATTCAACCA CAAGAACTAA

CAAAGTCAGA AAAATGGCTT CTATGATATC CTCTTCCGCT

GTGACAACAG TCAGCCGTGC TTCTAGGGTG CAATCCGCGG

CAGTGGCTCC ATTCGGCGGC CTGAAATCCA TGACTGGATT

CCCAGTGAAG AAGGTCAACA CTGACATTAC TTCCATTACA

AGCAATGGTG AAGAGTAAA GTGCATGCAG GTGTGGCCTC

CAATTGGAAA GAAGAAGTTT GAGACTCTTT CCTATTTGCC

ACCATTGACC atggctagcg acacgtacgc gggtgcttac gaccgtcagt cgcgcgagcg agaattcg agcgcagcaa gcccagcgac acagcgtagc gccaacgaag acaaggcggc cgaccttcag cgcgaagtcg agcgcgacgg gggccggttc aggttcgtcg ggcatttcag cgaagcgccg ggcacgtcgg cgttcgggac ggcggagcgc ccggagttcg aacgcatcct gaacgaatgc cgcgccgggc ggctcaacat gatcattgtc tatgacgtgt cgcgcttctc gcgcctgaag gtcatggacg cgattccgat tgtctcggaa ttgctcgccc tgggcgtgac
```

-continued

```
gattgtttcc actcaggaag gcgtcttccg gcagggaaac
gtcatggacc tgattcacct gattatgcgg ctcgacgcgt
cgcacaaaga atcttcgctg aagtcggcga agattctcga
cacgaagaac cttcagcgcg aattgggcgg gtacgtcggc
gggaaggcgc cttacggctt cgagcttgtt tcggagacga
aggagatcac gcgcaacggc cgaatggtca atgtcgtcat
caacaagctt gcgcactcga ccactcccct taccggaccc
ttcgagttcg agcccgacgt aatccggtgg tggtggcgtg
agatcaagac gcacaaacac cttcccttca agccgggcag
tcaagccgcc attcaccecgg gcagcatcac ggggctttgt
aagcgcatgg acgctgacgc cgtgccgacc cgggggcgaga
cgattgggaa gaagaccgct tcaagcgcct gggacccggc
aaccgttatg cgaatccttc gggacccgcg tattgcgggc
ttcgccgctg aggtgatcta caagaagaag ccggacggca
cgccgaccac gaagattgag ggttaccgca ttcagcgcga
cccgatcacg ctccggccgg tcgagcttga ttgcggaccg
atcatcgagc ccgctgagtg gtatgagctt caggcgtggt
tggacggcag ggggcgcggc aaggggctttt cccggggggca
agccattctg tccgccatgg acaagctgta ctgcgagtgt
ggcgccgtca tgacttcgaa gcgcggggaa gaatcgatca
aggactctta ccgctgccgt cgccggaagg tggtcgaccc
gtccgcacct gggcagcacg aaggcacgtg caacgtcagc
atggcggcac tcgacaagtt cgttgcggaa cgcatcttca
acaagatcag gcacgccgaa ggcgacgaag agacgttggc
```

```
gcttctgtgg gaagccgccc gacgcttcgg caagctcact
gaggcgcctg agaagagcgg cgaacgggcg aaccttgttg
cggagcgcgc cgacgccctg aacgcccttg aagagctgta
cgaagaccgc gcggcaggcg cgtacgacgg acccgttggc
aggaagcact tccggaagca acaggcagcg ctgacgctcc
ggcagcaagg ggcggaagag cggcttgccg aacttgaagc
cgccgaagcc ccgaagcttc cccttgacca atggttcccc
gaagacgccg acgctgaccc gaccggccct aagtcgtggt
ggggcgcgc gtcagtagac gacaagcgcg tgttcgtcgg
gctcttcgta gacaagatcg ttgtcacgaa gtcgactacg
ggcaggggc agggaacgcc catcgagaag cgcgcttcga
tcacgtgggc gaagccgccg accgacgacg acgaagacga
cgcccaggac ggcacggaag acgtagcggc gtagtctaga
gTCGAAGCAG ATCGTTCAAA CATTTGGCAA TAAAGTTTCT
TAAGATTGAA TCCTGTTGCC GGTCTTGCGA TGATTATCAT
ATAATTTCTG TTGAATTACG TTAAGCATGT AATAATTAAC
ATGTAATGCA TGACGTTATT TATGAGATGG GTTTTTATGA
TTAGAGTCCC GCAATTATAC ATTTAATACG CGATAGAAAA
CAAAATATAG CGCGCAAACT AGGATAAATT ATCGCGCGCG
GTGTCATCTA TGTTACTAGA TCGaccTGCAG
```

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. A transgenic plant comprising a phiC31 integrase and a selectable marker gene which are functional and present in plant plastids, said plastids comprising a nucleic acid encoding a heterologous protein of interest, wherein the nucleic acid is flanked by an attL and an attR site.

2. A method for producing the plant of claim 1, said method comprising the steps of
   a) providing a recipient plant having within its plastid genome a first att site recognized by phiC31 integrase, said att site being selected from the group consisting of attP and attB;
   b) introducing a phiC31 integrase into a plant cell obtained from the plant of step a) via a delivery method selected from the group consisting of
      1) transformation of the plant nucleus with a plasmid comprising a nucleic acid encoding said integrase operably linked to a nucleic acid encoding a plastid transit sequences, and
      2) transformation of the plastids of the plant cell with a nucleic acid encoding said integrase;
   c) introducing into said plant cell a DNA construct comprising at least one sequence encoding a heterologous protein of interest and a second att site recognized by said integrase, said att site being selected from the group consisting of attP and attB, said second att site being different from said first att site, and a selectable marker gene, wherein said integrase acts on said first and second att sites, thereby catalyzing insertion of said DNA construct into said plastid genome; and
   d) generating a plant from the plant cell of step c), said plant producing said heterologous protein of interest.

3. A transgenic plant comprising a) a phiC31 integrase which is functional and present in a plant plastid and b) transformed plastids comprising a nucleic acid encoding a heterologous protein of interest, wherein the nucleic acid is flanked by an attL and an attR site.

4. A method of producing the plant of claim 3, said method comprising the steps of
   a) providing a recipient plant having within its plastid genome a first att site recognized by phiC31 integrase, said att site selected from the group consisting of attP and attB;
   b) introducing a phiC31 integrase into a plant cell obtained from the plant of step a) via a delivery method selected from the group consisting of
      1) transformation of the plant nucleus with a plasmid comprising a nucleic acid encoding said integrase operably linked to a nucleic acid encoding a plastid transit sequence, and
      2) transformation of the plastids of the plant cell with a nucleic acid encoding said integrase;
   c) introducing into said plant cell a DNA construct comprising at least one sequence encoding a heterologous protein of interest and a second att site recognized by said integrase, wherein said att site is selected from the group consisting of attP and attB, said second att site being different from said first att site, wherein said integrase acts on said first and second att sites, thereby catalyzing insertion of said DNA construct into said plastid genome; and
   d) generating a plant from the plant cell of step c), said plant producing said heterologous protein of interest.

* * * * *